(12) United States Patent
Johnson

(10) Patent No.: US 8,562,994 B2
(45) Date of Patent: *Oct. 22, 2013

(54) HUMAN-MURINE CHIMERIC ANTIBODIES AGAINST RESPIRATORY SYNCYTIAL VIRUS

(75) Inventor: Leslie Sydnor Johnson, Darnestown, MD (US)

(73) Assignee: MedImmune, LLC, Gaithersburg, MD (US)

( * ) Notice: Subject to any disclaimer, the term of this patent is extended or adjusted under 35 U.S.C. 154(b) by 441 days.

This patent is subject to a terminal disclaimer.

(21) Appl. No.: 12/719,063

(22) Filed: Mar. 8, 2010

(65) Prior Publication Data

US 2012/0156195 A1 Jun. 21, 2012

Related U.S. Application Data

(60) Division of application No. 12/244,068, filed on Oct. 2, 2008, now Pat. No. 7,704,505, which is a division of application No. 11/198,322, filed on Aug. 8, 2005, now abandoned, which is a continuation of application No. 09/158,120, filed on Sep. 21, 1998, now abandoned, which is a division of application No. 08/290,592, filed on Aug. 15, 1994, now Pat. No. 5,824,307.

(51) Int. Cl.
*A61K 39/42* (2006.01)

(52) U.S. Cl.
USPC .................. 424/147.1; 424/130.1; 424/133.1

(58) Field of Classification Search
None
See application file for complete search history.

(56) References Cited

U.S. PATENT DOCUMENTS

| 4,659,563 | A |   | 4/1987 | Dobkin |   |
|---|---|---|---|---|---|
| 4,717,766 | A |   | 1/1988 | Dobkin |   |
| 4,800,078 | A |   | 1/1989 | Prince et al. |   |
| 5,071,758 | A |   | 12/1991 | Stott et al. |   |
| 5,183,657 | A |   | 2/1993 | Buurman |   |
| 5,194,595 | A |   | 3/1993 | Wathen |   |
| 5,219,996 | A |   | 6/1993 | Bodmer et al. |   |
| 5,223,254 | A |   | 6/1993 | Paradiso et al. |   |
| 5,225,539 | A |   | 7/1993 | Winter |   |
| 5,240,694 | A |   | 8/1993 | Gwaltney, Jr. |   |
| 5,288,630 | A |   | 2/1994 | Wathen |   |
| 5,290,540 | A |   | 3/1994 | Prince et al. |   |
| 5,332,567 | A |   | 7/1994 | Goldenberg |   |
| 5,693,762 | A | * | 12/1997 | Queen et al. | 530/387.3 |
| 5,824,307 | A | * | 10/1998 | Johnson | 424/133.1 |
| 6,818,216 | B2 | * | 11/2004 | Young et al. | 424/159.1 |

FOREIGN PATENT DOCUMENTS

| AT | 713113 | 11/1999 |
|---|---|---|
| CA | 2197684 | 2/1996 |
| EH | 0671927 | 9/1995 |
| EP | 0327378 | 8/1989 |
| EP | 0368684 | 5/1990 |
| WO | WO 90/07861 | 7/1990 |
| WO | WO 92/04381 | 3/1992 |
| WO | WO 92/05274 | 4/1992 |
| WO | WO 92/19244 | 11/1992 |
| WO | WO 93/05796 | 4/1993 |
| WO | WO 93/15199 | 8/1993 |
| WO | WO 93/15200 | 8/1993 |
| WO | WO 93/19197 | 9/1993 |
| WO | WO 93/20210 | 10/1993 |
| WO | WO 94/06448 | 3/1994 |
| WO | WO 94/17105 | 8/1994 |
| WO | WO 94/29351 | 12/1994 |

OTHER PUBLICATIONS

Paul Fundamental Immunology 3rd 1993, pp. 242, 292-295.*
Rudikoff PNAS vol. 79 pp. 1979-9183 1982.*
Coleman Reasearch Immunology 1994 vol. 145, pp. 33-36.*
Casset Biochem Biophys Research Com 2003, vol. 307, pp. 198-205.*
Tempest et al. 1991 Biotechnology vol. 9, pp. 266-271.*
Sigal et al., The Journal of Immunology 1987 vol. 139, pp. 1985-1990.*
Jones et al. Nature 1986 vol. 324, pp. 522-525.*
Beeler et al., Journal of Virology 1989 vol. 63, pp. 2941-2950.*
U.S. Appl. No. 07/813,372, filed Dec. 23, 1991, Johnson.
U.S. Appl. No. 09/158,120, filed Sep. 21, 1998, Johnson.
U.S. Appl. No. 11/198,322, filed Aug. 8, 2005, Johnson.
Ames et al., 1995, "Conversion of murine Fabs isolated from a combinatorial phage display library to full length immunoglobulins", J Immunol Methods.184(2):177.
Arbiza et al., 1992, "Characterization of two antigenic sites recognized by neutralizing monoclonal antibodies directed against the fusion glycoprotein of human respiratory syncytial virus", J Gen Virol. 73: 2225.
Balint and Larrick, 1993, "Antibody engineering by parsimonious mutagenesis", Gene. 137(1):109-118.
Beeler et al., 1989, "Neutralization Epitopes of the F Glycoprotein of Respiratory Syncytial Virus: Effect of Mutation Upon Fusion Function", J Virol. 63(7):2941-50.
Better et al., 1988, "*Escherichia coli* secretion of an active chimeric antibody fragment", Science. 240(4855):1041-3.
Boulianne et al., 1984, "Production of functional chimaeric mouse/human antibody", Nature 312(5995):643-646.
Burton and Barbas, 1994, "Human antibodies from combinatorial libraries", Adv. Immunol. 57:191-280.
Carson and Freimark, 1986., "Human lymphocyte hybridomas and monoclonal antibodies", Adv Immunol. 38:275-311.
Colman, 1994, "Effects of amino acid sequence changes on antibody-antigen interactions", Res Immunol. 145(1):33-6.

(Continued)

*Primary Examiner* — Mary E Mosher
*Assistant Examiner* — Myron Hill
(74) *Attorney, Agent, or Firm* — Mueting, Raasch & Gebhardt, P.A.

(57) ABSTRACT

This invention relates to a human antibody which contains the one CDR from each variable heavy and variable light chain of at least one murine monoclonal antibody, against respiratory syncytial virus which is MAb1129 and the use thereof for the prevention and/or treatment of RSV infection.

**

(56) References Cited

OTHER PUBLICATIONS

European Office Action of EP application No. 95928353, dated Feb. 28, 2002.
European Office Action of EP application No. 95928353, dated Feb. 20, 2006.
European Office Action of EP application No. 95928353 dated Jul. 27, 2005.
European Office Action of EP application No. 95928353 dated Mar. 6, 2003.
European Office Action of EP application No. 95928353, dated Mar. 31, 2004.
European Search Report of EP application No. 06003224.0, dated Dec. 19, 2008.
Foote et al., 1991. Kinetic maturation of an immune response. Nature 352:530-532.
Garcia-Barreno et al., 1989, "Marked Differences in the Antigenic Structure of Human Respiratory Syncytial Virus F and G Glycoproteins", J Virol. 63(2):925-32.
Gillies et al., 1989, "High-level expression of chimeric antibodies using adapted cDNA variable region cassettes", J Immunol Methods. 125:191-202.
Glaser et al., 1992, "Antibody engineering by codon-based mutagenesis in a filamentous phage vector system", J Immunol. 149:3903-3913.
Groothuis et al., 1988, "Respiratory Syncytial Virus Infection in Children with Bronchopulmonary Dysplasia", Pediatrics. 82(2):199-203.
Groothuis et al., 1993, "Prophylactic Administration of Respiratory Syncytial Virus Immune Globulin to High-risk Infants and Young Children. The Respiratory Syncytial Virus Immune Globulin Study Group", N Engl J Med. 329(21):1524-1530.
Hellstrom et al., 1987, "Antibodies for drug delivery", Controlled Drug Delivery, Fundamentals and Applications 2nd edition. Chapter 15: p. 623-653.
Hemming et al., 1985, "Studies of Passive Immunotherapy for Infections of Respiratory Syncytial Virus in the Respiratory Tract of a Primate Model", J Infect Dis. 152(5):1083-7.
Hemming et al., 1986, "Immunoglobulins in respiratory syncytial virus infections", Clinical Use of Intravenous Immunoglobulins, Morell and Nydegger., eds., Academic Press, London, pp. 285-294.
Japanese Office Action of JP application No. 2006-152600, dated Mar. 29, 2007.
Japanese Office Action of JP application No. 2006-152600, dated May 13, 2008.
Japanese Office Action of JP application No. 2006-152600, dated Oct. 7, 2008.
Japanese Office Action of JP application No. 2006-152600, dated Sep. 5, 2006.
Japanese Office Action of JP application No. 2006-152600, dated Sep. 28, 2007.
Japanese Office Action of JP application No. 2007-200866, dated Apr. 28, 2009.
Japanese Office Action of JP application No. 2007-200866, dated Jan. 7, 2009.
Japanese Office Action of JP application No. 2007-200866, dated Jan. 7, 2009 (Modified).
Japanese Office Action of JP application No. 2007-200866, dated May 7, 2008.
Japanese Office Action of JP application No. 2007-200866, dated Oct. 2, 2007.
Japanese Office Action of JP application No. 2008-227316, dated Dec. 9, 2008.
Japanese Office Action of JP application No. 2008-227316, dated Jul. 7, 2009.
Japanese Office Action of JP application No. 8-507450, dated Aug. 28, 2008.
Japanese Office Action of JP application No. 8-507450, dated Dec. 13, 2006.
Japanese Office Action of JP application No. 8-507450, dated Jan. 31, 2006.
Japanese Office Action of JP application No. 8-507450, dated Mar. 1, 2005.
Johnson et al., 1987, "The G Glycoprotein of Human Respiratory Syncytial Viruses of Subgroups A and B: Extensive Sequence Divergence Between Antigenically Related Proteins", Proc Natl Acad Sci USA. 84(16):5625-9.
Johnson et al., 1991, "Development of humanized monoclonal antibodies which neutralize respiratory syncytial virus", J Cellular Biochem Suppl. 15E. p. 120, Abstract No. 108.
Johnson et al., 1997, "Development ofa Humanized Monoclonal Antibody (MEDI.493) With Potent In Vitro and In Vivo Activity Against Respiratory Syncytial Virus", J Infect Dis. 176(5):1215-24.
Johnson et al., 1999, "A direct comparison of the activities of two humanized respiratory syncytial virus monoclonal antibodies: MEDI-493 and RSHZ19", J. Infect. Dis. 180(1):35-40.
Johnson, 1993, "Human-murine chimeric Abs to respiratory syncytial virus", NIAID Grant No. 5R44AI030300-02 Abstract http://crisp,cit.nih.gov/crisp/CRISP_LIB.getdoc?textkey=2065544&p_grant_num=2R44AI030300-02&P.
Johnson, 1994, "Human-murine chimeric Abs to respiratory syncytial virus", NIAID Grant No. 5R44AI030300-03 Abstract http://crisp,cit.nih.gov/crisp/CRISP_LIB.getdoc?textkey=2065544&p_grant_num=2R44AI030300-02&P.
Jones et al., 1986,"Replacing the complementarity-determining regions in a human antibody with those from a mouse", Nature 321:522-525.
Kudo et al., 1992, "New strategies to establish human monoclonal antibodies", Tohoku J Exp Med. 168(2):323-327.
Kudo et al., 1993, "Production of a human monoclonal antibody to a synthetic peptide by active in vivo immunization using a SCID mouse grafted with human lymphocytes", Yohoku J Exp Med. 171: 327-338.
Landry et al., Evaluation of reconstituted lyophilized palivizumab given intravenously at 15 and 30 mg/kg. Pediatric Research, 45 (4 Pt 2: 166A, 969) Annual Meeting of the American Pediatric Society and the Society for Pediatric Research, San Francisco, California, USA. May 1-4, 1999 Poster Session (poster 87).
Langer, 1990, "New methods of drug delivery", Science. 249:1527-1533.
Lee F. et al., 1992. Calculations of Antibody-Antigen Interactions: Microscopic and semi-microscopic evaluation of the free energies of binding of phophorylcholine analogs to McPc603, Protein Engineering vol. 5 No. 3 pp. 215-222.
Liu et al., 1987, "Expression of mouse::human immunoglobulin heavy-chain cDNA in lymphoid cells", Gene 54(1):33-40.
Lobuglio et al., 1989, "Mouse/human chimeric monoclonal antibody in man: kinetics and immune response", Proc Natl Acad Sci USA. 86(11):4220-4224.
Marks et al., 1992, "By-passing immunization: building high affinity human antibodies by chain shuffling", Biotechnology (NY) 10(7):779-83.
Medimmune, Inc, 1999 SYNAGIS (registered trademark) package insert, revised Dec. 2, 1999.
Medimmune, SYNAGIS (registered trademark) package insert, last revised Oct. 23, 2002.
Meissner et al., 1999, "Safety and pharmacokinetics of an intramuscular monoclonal antibody (SB 209763) against respiratory syncytial virus (RSV) in infants and young children at risk for severe RSV disease", Antimicrob Agents Chemother. 43(5):1183-8.
Morell et al., 1986, "Clinical Use of Intravenous Immunoglobulins", Academic Press, London, pp. 285-294.
Morrison et al., 1984, "Chimeric human antibody molecules: mouse antigen-binding domains with human constant region domains", Proc. Natl. Acad. Sci. USA 81(21):6851-6855.
Morrison et al., 1985, "Transfectomas provide novel chimeric antibodies", Science 229(4719):1202.
Mullinax et al., 1992, "Expression of a heterodimeric Fab antibody protein in one cloning step", Bio Techniques. 12:864-869.
Murphy et al., 1988, "Passive Transfer of Respiratory Syncytial Virus (RSV) Antiserum Suppresses the Immune Response to the RSV Fusion (F) and Large (G) Glycoproteins Expressed by Recombinant Vaccinia Viruses", J Virol. 62(10):3907-10.

(56) References Cited

OTHER PUBLICATIONS

Murphy et al., 1991, "Effect of Passive Antibody on the Immune Response of Cotton Rats to Purified F and G HG Glycoproteins of Respiratory Syncytial Virus (RSV)", Vaccine. 9(3):185-9.
Newman et al., 1992, "'Primatization' of recombinant antibodies for immunotherapy of human diseases: A Macaque/Human chimeric antibody against human CD4", Biotechnol. 10:1455-1460.
Office Action of U.S. Appl. No. 08/290,592, dated Apr. 13, 1998.
Office Action of U.S. Appl. No. 08/290,592, dated Apr. 30, 1998.
Office Action of U.S. Appl. No. 08/290,592, dated Feb. 4, 1998.
Office Action of U.S. Appl. No. 08/290,592, dated Jan. 23, 1998.
Office Action of U.S. Appl. No. 08/290,592, dated Jul. 21, 1997.
Office Action of U.S. Appl. No. 08/290,592, dated Nov. 24, 1995.
Office Action of U.S. Appl. No. 09/158,120, dated Apr. 20, 2004.
Office Action of U.S. Appl. No. 09/158,120, dated Apr. 26, 2000.
Office Action of U.S. Appl. No. 09/158,120, dated Aug. 23, 2005.
Office Action of U.S. Appl. No. 09/158,120, dated Feb. 9, 2005.
Office Action of U.S. Appl. No. 09/158,120, dated Jan. 16, 2001.
Office Action of U.S. Appl. No. 09/158,120, dated Jan. 13, 2003.
Office Action of U.S. Appl. No. 09/158,120, dated Mar. 6, 2002.
Office Action of U.S. Appl. No. 11/198,322, dated Dec. 8, 2008.
Office Action of U.S. Appl. No. 11/198,322, dated May 6, 2008.
Padlan, 1991, "A possible procedure for reducing the immunogenicity of antibody variable domains while preserving their ligand-binding properties", Mol. Immunol. 28(4/5):489-498.
Palomo et al., 1990, "Induction of a Nutralizing Immune Response to Human Respiratory Syncytial Virus with Anti-Idiotypic Antibodies", J. Virology 64(9): 4199-4206.
Prince et al., 1983, "Mechanisms of Immunity to Respiratory Syncytial Virus in Cotton Rats", Infect Immun. 42(1):81-7.
Prince et al., 1985, "Quantitative Aspects of Passive Immunity to Respiratory Syncytial Virus Infection in Infant Cotton Rats.", J Virol. 55(3):517-20.
Prince et al., 1985, "Immunoprophylaxis and Immunotherapy of Respiratory Syncytial Virus Infection in the Cotton rat", Virus Res. 3(3):193-206.
Riechmann et al., 1988, "Reshaping human antibodies for therapy", Nature. 332(6162):323-7.
Roguska et al., 1994, "Humanization of murine monoclonal antibodies through variable domain resurfacing", Proc. Natl. Acad. Sci. U.S.A. 91(3):969-973.
Roitt et al., 1991, "The recognition of antigen 1-primary interaction", Essential Immunology 4:65-83.
Rudikoff et al., 1982, "Single amino acid substitution altering antigen-binding specificity", Proc. Natl. Acad. Sci. USA 79(6):1979-1983.
Sahagan et al., 1986, "A genetically engineered murine/human chimeric antibody retains specificity for human tumor-associated antigen", J. Immunol. 137(3):1066-1074.
Seaver, 1994, "Monoclonal antibodies in industry: More difficult than originally thought", Genetic Engineering News, vol. 14, No. 14, p. 10 and 21.
Sevier et al., 1981, "Monoclonal antibodies in clinical immunology", Clin Chem. 27(11):1797-806.
Sorbera et al., 1998. Palivizumab. Drug Data Report 20:702-703.
Sorbera et al., 1998. Palivizumab. Drugs of the Future 23:970-976.
Steplewski et al., 1988, "Biological activity of human-mouse IgG1, IgG2, IgG3, and IgG4 chimeric monoclonal antibodies with antitumor specificity", Proc. Natl. Acad. Sci. USA 85(13):4852-4856.
Stott et al., 1984, "The characterization and uses of monoclonal antibodies to respiratory syncytial virus", Dev Biol Stand. 57:237-44.
Studnicka et al., 1994, "Human-engineered monoclonal antibodies retain full specific binding activity by preserving non-CDR complementarity-modulating residues", Protein Eng. 7:805-814.
Sun et al., 1987, "Chimeric antibody with human constant regions and mouse variable regions directed against carcinoma-associated antigen 17-1A", Proc. Natl. Acad. Sci. USA. 84(1):214-218.
Takahashi et al. 1984, "Rearranged immunoglobulin heavy chain variable region (VH) pseudogene that deletes the second complementarity-determining region", Proc. Natl. Acad. Sci, USA. 81: 5194-198.
Takeda et al., 1985, "Construction of chimaeric processed immunoglohulin genes containing mouse variable and human constant region sequences", Nature 314(6010):452-454.
Talwar et al., 1976, "Isoimmunization against human chorionic gonadotropin with conjugates of processed beta-subunit or the hormone and tetanus toxoid", Proc. Natl. Acad. Sci. USA. 73(1):218-222.
Taylor et al., 1984, "Monoclonal antibodies protect against respiratory syncytial virus infection in mice", Immunology. 52(1):137-42.
Taylor et al., 1992, "Protective epitopes on the fusion protein of respiratory syncytial virus recognized by murine and bovine monoclonal antibodies", J Gen Virol. 73 ( Pt 9):2217-23.
Tempest et al., 1991, "Reshaping a human monoclonal antibody to inhibit human respiratory syncytial virus infection in vivo", Biotechnology 9:266-271.
The Impact-RSV Study Ciroup, 1998. Palivizumab, a humanized respiratory syncytial virus monoclonal antibody, reduces hospitalization from respiratory syncytiai virus infection in high-risk infants. Pediatrics. 102(3 Pt 1):531-537.
Walsh et al., 1984, "Protection from respiratory syncytial virus infection in cotton rats by passive transfer of monoclonal antibodies", Infect Immun. 43(2):756-8.
Walsh et al., 1987, "Immunization with Glucoprotein Subunits of Respiratory Syncytial Virus to Protect Cotton Rats Against Viral Infection", J Infect Dis. 155(6): 1198-204.
Walsh et al., 1989, "Comparison of antigenic sites of subtype-specific respiratory syncytial virus attachment proteins", Journal of General Virology 70:2953-2961.
Ware et al., 1985, "Human, rat or mouse hybridomas secrete high levels of monoclonal antibodies following transplantation into mice with severe combined immunodeficiency disease (SCID)", J Immunol Methods. 85(2):353-61.
Weltzin et al., 1994, "Intranasal Monoclonal Immunoglobulin A against Respiratory Syncytial Virus Protects against Upper and Lower Respiratory Tract Infections in Mice", Antimicro Agents & Chemo. 38(12):2785-2791.
Winter et al., 1993, "Humanized antibodies", Immunology Today 14(6):243-246.
Declaration of Leslie S. Johnson Under 37 CFR 1.131, dated May 16, 1996 with Exhibits 1-4.
Declaration of Leslie S. Johnson Under 37 CFR 1.132, dated May 16, 1996 with Exhibits 1-2.
Declaration Under Rule 132, dated Mar. 12, 198 with Exhibits 1-2.

\* cited by examiner

FIG. IA

```
                    5                              10
Gln Val Gln Leu Val Gln Ser Gly Ala Glu Val Lys

Gln Val Gln Leu Val Gln Ser Gly Ala Glu Val Lys
 *               *                         *   *
Glu Val Gln Leu Gln Gln Ser Gly Ala Glu Leu Val 25                             30
Ser Cys Lys Ala Ser Gly Tyr Thr Phe Asn Ser Tyr
                         *   *   *   *   *
Ser Cys Lys Ala Ser Gly Phe Asn Ile Lys Asp Tyr

Ser Cys Lys Ala Ser Gly Phe Asn Ile Lys Asp Tyr 45                             50
Pro Gly Gln Gly Leu Glu Trp Met Gly Ile Ile Asn
                             *       *       *
Pro Gly Gln Gly Leu Glu Trp Ile Gly Trp Ile Asp
 *                          ─────────────────────
                                              CDR
Pro Glu Gln Gly Leu Glu Trp Ile Gly Trp Ile Asp 65                             70
Ala Gln Lys Phe Gln Gly Arg Val Thr Met Thr Arg
 *   *                  ─────────────────────────
Asp Pro Lys The Gln Gly Arg Val Thr Met Thr Arg
                             *   *   *   *   *
Asp Pro Lys Phe Gln Gly Lys Ala Ser Ile Thr Ser
─────────────────────────

85                             90
    Glu Leu Ser Ser Leu Arg Ser Glu Asp Thr Ala

Met Glu Leu Ser Ser Leu Arg Ser Glu Asp Thr Ala
 *                       *
Leu Gln Leu Ser Ser Leu Thr Ser Glu Asp Thr Ala 105                            110
 -   -   -   -   -   -   -   -   -   -   -   -

Thr Ser Ser Phe Asp Phe Trp Gly Gln Gly Thr Thr
─────────────────────
        CDR 3
Thr Ser Ser Phe Asp Phe Trp Gly Gln Gly Thr Thr
            / J>>
```

FIG. 1B

|  |  | 15 |  |  |  | 20 |  |  |
|---|---|---|---|---|---|---|---|---|
| Lys | Pro | Gly | Ala | Ser | Val | Lys | Val | Human HV3 VH |
| Lys | Pro | Gly | Ala | Ser | Val | Lys | Val | "CDR Grafted" VH |
| * |  |  |  | * |  |  | * |  |
| Arg | Pro | Gly | Ala | Leu | Val | Lys | Leu | Murine 1308F VH |

|  |  | 35 |  |  |  | 40 |  |
|---|---|---|---|---|---|---|---|
| Tyr | Met | His | Trp | Val | Arg | Gln | Ala |
|  | * | * |  |  |  |  |  |
| Tyr | Ile | Tyr | Trp | Val | Arg | Gln | Ala |
|  | CDR 1 |  |  |  | * |  | * |
| Tyr | Ile | Tyr | Trp | Val | Lys | Gln | Arg |

|  |  | 55 |  |  |  | 60 |
|---|---|---|---|---|---|---|
| Pro | Ser | Gly | Gly | Ser | Thr | Ser | Tyr |
|  | * | * |  | * |  | * | * |
| Pro | Glu | Asn | Gly | Asn | Thr | Val | Phe |
| 2 |  |  |  |  |  |  |  |
| Pro | Glu | Asn | Gly | Asn | Thr | Val | Phe |

|  |  | 75 |  |  |  | 80 |
|---|---|---|---|---|---|---|
| Asp | Thr | Ser | Thr | Ser | Thr | Val | Tyr |
| Asp | Thr | Ser | Thr | Ser | Thr | Val | Tyr |
|  |  |  | * | * |  | * |  |
| Asp | Thr | Ser | Ser | Asn | Thr | Ala | Tyr |

|  |  | 95 |  |  |  | 100 |  |
|---|---|---|---|---|---|---|---|
| Val | Tyr | Tyr | Cys | Ala |  |  |  |
| Val | Tyr | Tyr | Cys | Ala | Tyr | Tyr | gly |
| Val | Tyr | Tyr | Cys | Ala | Tyr | Tyr | Gly |
|  |  |  | <<V | / | D |  |  |
|  |  | 115 |  |  |  |  |  |
| – | – | – | – | – |  |  |  |
| Leu | Thr | Val | Ser | Ser |  |  |  |
| Leu | Thr | Val | Ser | Ser |  |  |  |

FIG. 2A

```
                    5                              10
Asp Ile Gln Met Thr Gln Ser Pro Ser Thr Leu Ser

Asp Ile Gln Met Thr Gln Ser Pro Ser Thr Leu Ser
        *                          *   *   *
Asp Ile Lys Met Thr Gln Ser Pro Ser Ser Met Tyr 25                              30
Ile Thr Cys Arg Ala Ser Gln Ser Ile Ser Ser Trp
            *                *       *   *   *
Ile Thr Cys Lys Ala Ser Gln Asp Ile Asn Arg Tyr
                           CDR 1
Ile Thr Cys Lys Ala Ser Gln Asp Ile Asn Arg Tyr 45                              50
Gly Lys Ala Pro Lys Leu Leu Ile Tyr Asp Ala Ser
                                    *       *
Gly Lys Ala Pro Lys Leu Leu Ile Tyr Arg Ala Asn
        *               *           *
Gly Lys Ser Pro Lys Thr Leu Ile His Arg Ala Asn 65                              70
Arg Phe Ser Gly Ser Gly Ser Gly Thr Glu Phe Thr

Arg Phe Ser Gly Ser Gly Ser Gly Thr Glu Phe Thr
                                *       *   *
Arg PHE Ser Gly Ser Gly Ser Gly Gln Glu Tyr Ser 85                              90
Asp Asp Phe Ala Thr Tyr Tyr Cys Gln Gln Tyr Asn
                                *       *   *
Asp Asp Phe Ala Thr Tyr Tyr Cys Leu Gln Phe His
*   *   *   *
Glu Asp Met Gly Ile Tyr Tyr Cys Leu Gln Phe His

105
  -   -   -   -   -   -   -

Gly Thr Lys Leu Glu Ile Lys

Gly Thr Lys Leu Glu Ile Lys
```

FIG. 2B

```
                      15                        20
         Ala Ser Val GLY Asp Arg Val Thr - Human K102 VL Ala Ser Val Gly Asp Arg Val Thr - "CDR Grafted" VL
          *       *        *
         Val Ser Leu Gly Glu Arg Val Thr - Murine 1308F VL 35                        40
         Leu Ala Trp Tyr Gln Gln Lys Pro
              *
         Leu Asn Trp Tyr Gln Gln Lys Pro
         ─────────        *
         Leu Asn Trp Phe Gln Gln Lys Pro 55                        60
         Ser Leu Glu Ser Gly Val Pro Ser
          *       *   *
         Arg Leu Val Asp Gly Val Pro Ser
         ─────────────────
           CDR 2
         Arg Leu Val Asp Gly Val Pro Ser 75                        80
         Leu Thr Ile Ser Ser Leu Gln Pro Leu Thr Ile Ser Ser Leu Gln Pro
                                        *
         Leu Thr Ile Ser Ser Leu Glu Phe 95                       100
         Ser Tyr Ser  -   -   -
          *   *   *
         Glu Phe Pro Tyr Thr Phe Gly Gly
         ─────────────────────
           CDR 3
         Glu Phe Pro Tyr Thr Phe Gly Gly
                  <<V / J>>
```

FIG. 3A

5' gcgaattccatggactggacctggagggtc 3'

```
         MetAspTrpThrTrpArgValPheCysLeuLeuAlaValAlaAlaProGlyAlaHisSerGln
5'    CCATGGACTGGACCTGGAGGGTCTTCTGCTTGCTTGTTGCTGTAGCACCAGGTGCCCACTGCCAG
   1  ----+----+----+----+----+----+----+----+----+----+----+----+----
3'    TACCTGACCTGGACCTCCCAGAAGACGAACGACCGACATCGTGGTCCACGGGTGACGGGTC

ValGlnLeuValGlnSerGlyAlaGluValLysLysProGlyAlaSerValLysValSer
      GTGCAGTGGTGCAGTCTGGAGCTGAGGTGAAGAAGCCTGGAGCCTCAGTGAAGGTTTCC
  61  ----+----+----+----+----+----+----+----+----+----+----+----
      CACGTCGACCACGTCAGACCTCGACTCCACTTCTTCGGACCTCGGAGTCACTTCCAAAGG

CysLysAlaSerGlyPheAsnIleLysAspTyrTyrIleTyrTrpValArgGlnAlaPro
      TGCAAGGCATCTGGATTCAACATTAAGGACTACTACATTTACTGGGTGCGACAGGCTCCT
 121  ----+----+----+----+----+----+----+----+----+----+----+----
      ACGTTCCGTAGACCTAAGTTGTAATTCCTGATGATGTAAATGACCCACGCTGTCCGAGGA

GlyGlnGlyLeuGluTrpMetGlyTrpIleAspProGluAsnGlyAsnThrValPheAsp
      GGACAAGGGCTCGAGTGGATGGGTTGGATTGACCCTGAGAATGGTAATACTGTGTTTGAC
 181  ----+----+----+----+----+----+----+----+----+----+----+----
      CCTGTTCCCGAGCTCACCTACCCAACCTAACTGGACTCCTTACCATTATGACACAAACTG
```

FIG. 3B

```
     ProLysPheGlnGlyArgValThrMetThrArgAspThrSerThrValTyrMet
     CCGAAGTTCCAGGGCAGAGTCACCATGACCAGGGACACGTCCACGAGCAGTCTACATG
241  ---------+---------+---------+---------+---------+---------+
     GGCTTCAAGGTCCCCGTCTCAGTGGTACTGGTCCCTGTGCAGGTGCTCGTCAGATGTAC

GluLeuSerLeuArgSerGluAspThrAlaValTyrTyrCysAlaValTyrTyrGlyThr
     GAGCTGAGCCTGAGATCTGAGGACACGGCCGTGTATTACTGTGCCGTACTACGGTACA
301  ---------+---------+---------+---------+---------+---------+
     CTCGACTCGGACTCTAGACTCCTGTGCCGGCACATAATGACACGGCATGATGCCATGT

SerSerPheAspPheTrpGlyGlnGlyThrThrLeuThrValSerSer
     AGCTCCTTTGACTTCTGGGGCCAAGGCACCACTCTCACAGTGAGCTCA
361  ---------+---------+---------+---------+---------+
     TCGAGGAAACTGAAGACCCCGGTTCCGTGGTGAGAGTGTCACTCGAGTattcctagg 5'
                                                  3'ggtgagagtgtcactcgagtattcctagggc 5'
```

FIG. 4A

```
cgcggatccatggacatggagggtcccc
         MetAspMepArgValProAlaGlnLeuLeuGlyLeuLeuLeuLeuTrpLeuProGlyAla
ccATGGACATGGAGGGTCCCCGCGCTCAGCAGCTCCTGGGGCTCCTGCTGCTGCTTCTGGCTCTCCCAGGTGCC
 1 ---------+---------+---------+---------+---------+---------+----
   TACCTGTACTCCCAGGGGGCGAGTCGAGGACCCCGAGGACGACGAGACCGAGGTCCACGG LysCysAspIleGlnMetThrGlnSerProSerThrLeuSerAlaSerValGlyAspArg
   AAATGTGATATCCAGATGACCCAGTCTCCTTCCACCCTGTCTGCATCTGTAGGAGACAGA
 61 ---------+---------+---------+---------+---------+---------+----
   TTTACACTATAGGTCTACTGGGTCAGAGGAAGGTGGGACAGACGTAGACATCCTCTGTCT ValYhrIleThrCysLysAlaSerGlnAspIleAsnArgTyrLeuAsnTrpTyrGlnGln
   GTCACCATCACTTGCAAGGCGAGTCAGGACATTAATAGGTAGTTAAACTGGTACCAGCAG
121 ---------+---------+---------+---------+---------+---------+----
   CAGTGGTAGTGAACGTTCCGCTTAGTCCTGTAATTATCCATCAATTTGACCATGGTCGTC LysProGlyLysAlaProLysLeuLeuIleTyrArgAlaAsnArgLeuValAspGlyVal
   AAACCCGGGAAAGCCCCTAAGCTCCTGATCTATCGTGCAAACAGATTGGTAGATGGGGTC
181 ---------+---------+---------+---------+---------+---------+----
   TTTGGGCCCTTTCGGGGATTCGAGGACTAGATAGCACGTTTGTCTAACCATCTACCCCAG
```

FIG. 4B

```
     ProSerArgPheSerGlySerGlyThrGluPheThrLeuThrIleSerSerLeu
241  CCATCAAGGTTCAGCGGGCAGTGGGACAGAATTCACTCTCACCATCAGCAGCCTG
     ------+---------+---------+---------+---------+---------+
     GGTAGTTCCAAGTCGCCCGTCACCCTGTCTTAAGTGAGAGTGGTAGTCGTCGGAC

GlnProAspAspPheAlaThrTyrTyrCysLeuGlnPheHisGluPheProTyrThrPhe
301  CAGCCTGATGATTTTGCAACTTATTACTGCCTACAGTTTCATGAGTTTCCGTACACGTTC
     ------+---------+---------+---------+---------+---------+
     GTCGGACTACTAAAACGTTGAATAATGACGGATGTCAAAGTACTCAAAGGCATGTGCAAG

GlyGlyGlyThrLysLeuGluIleLys
361  GGAGGGGGGACCAAGCTTGAAATAAAA      3'
     ------+---------+---------+      gtgcaag
     CCTCCCCCCTGGTTCGAACTTTATTTT      5'
                                      cctccccctggttcgaaccc 5'
```

FIG. 7A

```
                    5                  10                 15
 1  Gln Val Thr Leu Arg Glu Ser Gly Pro Ala Leu Val Lys Pro Thr   Human VH (Cor)
    Gln Val Thr Leu Arg Glu Ser Gly Pro Ala Leu Val Lys Pro Thr   "Humanized" VH
                    *                      *   *
    Gln Val Glu Leu Gln Glu Ser Gly Pro Gly Ile Leu Gln Pro Ser   Murine 1129 VH 16  Gln Yhr Leu Thr Cys Thr Phe Ser Gly Phe Ser Leu Ser
    Gln Thr Leu Thr Cys Thr Phe Ser Gly Phe Ser Leu Ser
             *
    Gln Thr Leu Ser Leu Thr Cys Ser Phe Ser Gly Phe Ser Leu Ser 31  Ser Ser Gly Met Cys Val Gly Trp Ile Arg Gln Pro Pro Gly Lys
                    *
    Thr Ser Gly Met Ser Val Gly Trp Ile Arg Gln Pro Pro Gly Lys
                                                             *
    Thr Ser Gly Met Ser Val Gly Trp Ile Arg Gln Pro Ser Gly Glu 46  Ala Leu Glu Trp Leu Ala Asp Ile Glu Trp Asp Asp Asp Lys Asp
                                                         *
    Ala Leu Glu Trp Leu Ala Asp Ile Trp Trp Asp Asp Asp Lys Asp
                            *
    Gly Leu Glu Trp Leu Ala Asp Ile Trp Trp Asp Asp Asp Lys Asp
```

FIG. 7B

```
    Tyr Asn Thr Ser Leu Asp Thr Arg Leu Thr Ile Ser Lys Asp Thr
                         *
 61 Tyr Asn Pro Ser Leu Lys Ser Arg Leu Thr Ile Ser Lys Asp Thr
                     *
    Tyr Asn Pro Ser Leu Lys Ser Arg Leu Thr Ile Ser Lys Asp Thr

Swe Lys Asn Gln Val Val Leu Thr Val Thr Asn Met Asp Pro Ala
                                     *
 76 Ser Lys Asn Gln Val Leu Lys Val Thr Asn Met Asp Pro Ala
                         *                       *
    Ser Ser Asn Gln Val Phe Leu Lys Ile Thr Gly Val Asp Thr Ala

Asp Thr Ala Thr Tyr Tyr Cys Ala Arg Ile Yhr Val Ile Pro Ala Pro Ala Gly
                                                 *       *
 91 Asp Thr Ala Thr Tyr Tyr Cys Ala Arg Ser Met Ile Thr Asn Trp
                                     *                   *
    Asp Thr Ala Thr Tyr Tyr Cys Ala Arg Ser Met Ile Thr Asn Trp

Tyr Met Asp Val Trp Gly Arg Gly Thr Pro Val Thr Val Ser Ser
     *                           *                *
106 Tyr Phe Asp Val Trp Gly Ala Gly Thr Thr Val Thr Val Ser Ser

Tyr Phe Asp Val Trp Gly Ala Gly Thr Thr Val Thr Val Ser Ser
```

FIG. 8A

```
                   5                  10                 15
Asp Ile Gln Met Thr Gln Ser Pro Ser Thr Leu Ser Ala Ser Val    - Human K102 VL
 -                                                                 (SEQ ID 33)
Asp Ile Gln Met Thr Gln Ser Pro Ser Thr Leu Ser Ala Ser Val    - "CDR Grafted" VL
             *                                         *           (SEQ ID 34)
Asp Ile Gln Leu Thr Gln Ser Pro Ala Ile Met Ser Ala Ser Pro    - Murine 1129 VL
                                                                   (SEQ ID 35)
                   20                 25                 30
Gly Asp Arg Val Thr Ile Thr Cys Arg Ala Ser Gln Ser Ile Ser
                         *       *                    *   *
Gly Asp Arg Val Thr Ile Thr Cys Lys Cys Gln Leu Ser Val Gly
     *   *           *                                 
Gly Glu Lys Val Thr Met Thr Cys Lys Cys Gln Leu Ser Val Gly
                                 └────────CDR 1─────────┘
                   35                 40                 45
Ser Trp Leu Ala Trp Tyr Gln Gln Lys Pro Gly Lys Ala Pro Lys
 *
Tyr Met His Trp Tyr Gln Gln Lys Pro Gly Lys Ala Pro Lys
 └──────┘
Tyr Met His Trp Tyr Gln Gln Lys Ser Ser Thr Ser Pro Lys
                                 *
                   50                 55                 60
Leu Leu Ile Tyr Asp Ala Ser Ser Leu Glu Ser Gly Val Pro Ser
                     *                   *
Leu Trp Ile Tyr Asp Thr Ser Lys Leu Ala Ser Gly Val Pro Ser
     └────────CDR 2────────┘
Leu Trp Ile Tyr Asp Thr Ser Lys Leu Ala Ser Gly Val Pro Gly
```

FIG. 8B

```
                65              70              75
Arg Phe Ser Gly Ser Gly Ser Gly Thr Glu Phe Thr Leu Thr Ile
 *
Arg Phe Ser Gly Ser Gly Ser Gly Thr Glu Phe Thr Leu Thr Ile
                               *       *
Arg Phe Ser Gly Ser Gly Ser Gly Asn Ser Tyr Ser Leu Thr Ile
                         80                      85              90
Ser Ser Leu Gln Pro Asp Asp Phe Ala Thr Tyr Tyr Cys Gln Gln
                     *
Ser Ser Leu Gln Pro Asp Asp Phe Ala Thr Tyr Tyr Cys Phe Gln
 *                   *                                   ————————
Ser Ser Ile Gln Ala Glu Asp Val Ala Thr Tyr Tyr Cys Phe Gln
             95                                  100             105
Tyr Asn Ser Tyr Ser
 *           *
Gly Ser Gly Tyr Pro Phe Thr Phe Gly Gly Gly Thr Lys Leu Glu Ile Lys
——————————————————————————
         CDR 3
Gly Ser Gly Tyr Pro Phe Thr Phe Gly Gly Gly Thr Lys Leu Glu Ile Lys

```
SJ153  5'-GGCGTCGACTCACC-
          ATGGACTGGACCTGGAGGGTCTTCTGCTTGCTGTAGCACCAGGTGCCACTCCC-3'
                                                    SJ150 5'-CCAG
    1   ----+----+----+----+----+----+----+----+----+----+----+----+    60

MetAspTrpThrTrpArgValPheCysLeuLeuAlaValAlaProGlyAlaHisSerGln

GTCACCTTAAGGGAGTCTGGTCCTGCCCTGGTGAAACCCACAGACCCTCACACTGACC
   61   ----+----+----+----+----+----+----+----+----+----+----+----+   120
                                                  3'-GGAGTGTGACTGG

ValThrLeuArgGluSerGlyProAlaLeuValLysProThrGlnThrLeuThr

TGCACC-3'                                        SJ151 5'- CAG
  121   ----+----+----+----+----+----+----+----+----+----+----+----+   180
        ACGTGGAAGAGACCCAAAAGTGACTCGTGAAGACCATACTCACATCCGACCTAAGCAGTC

CysThrPheSerLeuSerThrSerGlyMetSerValGlyTrpIleArgGln

CCCCCAGGGAAGGCCCTGCACTCGCTTGCAGACATTTGGTGGGATGACAAAAGGACTAT
  181   ----+----+----+----+----+----+----+----+----+----+----+----+   240
        GGGGGTCCCTTCCGGG-5' SJ149                        3'- GATA

ProProGlyLysAlaLeuGluTrpLeuAlaAspIleTrpTrpAspAspLysLysAspTyr
```

FIG. 9B

```
                                                    SJ152 5'-GGTC
        AATCCATCCCTGAAG-3'                               |    |
241     ---------------+---------+---------+---------+---------+     300
        TTAGGTACCGACTTCTCGGCCGAGTGTTAGAGGTTCCTATGGAGGTTTTTGGTCCACCAG

AsnProSerLeuLysSerArgLeuThrIleGerLysAspThrSerLysAsnGlnValVal

CTTAAAAGTGACCAACATGGACTCCTGCTGATACTGCCACTTACTACTGTGCTCGGTCTATG
301     ---------+---------+---------+---------+---------+---------+     360
        GAATTTCACTGGTTG-5' SJ148                                    3'-TAC

LeuLysValThrAsnMetAspProAlaAspThrAlaThrTyrTyrCysAlaArgSerMet

417  SJ147
361     ---------+---------+---------+---------+---------+---------+        5' SJ147
        TAGTGCTTGACCATGAAGCTACAGAACCCCGCCCTGGTGCCAGTGGCACTGGAGTCCG-5' SJ147

IleThrAsnTrpTyrPheAspValTrpGlyAlaGlyThrThrValThrValSerSer
```

US 8,562,994 B2

HUMAN-MURINE CHIMERIC ANTIBODIES AGAINST RESPIRATORY SYNCYTIAL VIRUS

This application is a divisional of U.S. application Ser. No. 12/244,068 filed Oct. 2, 2008, now issued as U.S. Pat. No. 7,704,505, which is a divisional of U.S. application Ser. No. 11/198,322 filed on Aug. 8, 2005 (abandoned), which is a continuation of U.S. application Ser. No. 09/158,120 filed on Sep. 21, 1998 (abandoned), which is a divisional of U.S. application Ser. No. 08/290,592 filed on Aug. 15, 1994, now issued as U.S. Pat. No. 5,824,307, each of which is incorporated by reference in their entireties.

BACKGROUND

Respiratory syncytial virus (RSV) is the major cause of acute respiratory illness in young children admitted to hospitals, and the community practice will treat perhaps five times the number of hospitalized children. It is therefore, the most common cause of lower respiratory tract infection in young children. While the majority of community-acquired RSV infections resolve themselves in a week to ten days, many hospitalized children, especially under six months of age require assisted ventilation.

Efforts to produce an effective vaccine have been unsuccessful (8). A major obstacle to vaccine development is safety; the initial formalin inactivated RSV vaccine caused an increased incidence of RSV lower respiratory tract disease and death in immunized children upon exposure to virus (5).

Recently, the drug ribavirin has been licensed for therapy of RSV pneumonia and bronchiolitis (2,3); its value is controversial (4). Although ribavirin has shown efficacy (9), the drug has to be administered over an 18 hour period by aerosol inhalation. In addition, the level of secondary infections following cessation of treatment is significantly higher than in untreated patients.

Studies have shown that high-titered RSV immunoglobulin was effective both in prophylaxis and therapy for RSV infections in animal models (6, 7). Infected animals treated with RSV immune globulin, showed no evidence of pulmonary immune-complex disease (6, 7).

Even if RSV hyperimmune globulin is shown to reduce the incidence and severity of RSV lower respiratory tract infection in high risk children, several disadvantages may limit its use. One drawback is the necessity for intravenous infusion in these children who have limited venous access because of prior intensive therapy. A second disadvantage is the large volume of RSVIG required for protection, particularly since most these children have compromised cardiopulmonary function. A third disadvantage is that intravenous infusion necessitates monthly hospital visits during the RSV season which places these children at risk of nosocomial RSV infection (1). A final problem is that it may prove to be very difficult to select sufficient donors to produce a hyperimmune globulin for RSV to meet the demand for this product. Currently only about 8% of normal donors have RSV neutralizing antibody titers high enough to qualify for the production of hyperimmune globulin.

Another approach may be the development of monoclonal antibodies with high specific neutralizing activity as an alternative to hyperimmune globulin. It is preferable, if not necessary, to use human monoclonal antibodies rather than murine or rat antibodies to minimize the development of human anti-rodent antibody responses which may compromise the therapeutic efficacy of the antibody or induce immune-complex pathology. However, the generation of human monoclonal antibodies with the desired specificity may be difficult and the level of production from human cell lines is often low, precluding their development.

An alternative approach involves the production of human-mouse chimeric antibodies in which the genetic information encoding the murine heavy and light chain variable regions are fixed to genes encoding the human heavy and light constant regions. The resulting mouse-human hybrid has about 30% of the intact immunoglobulin derived from murine sequences. Therefore, although a number of laboratories have constructed chimeric antibodies with mouse variable and human constant domains (10-18), the mouse variable region may still be seen as foreign (19).

SUMMARY OF THE INVENTION

It is therefore an object of the present invention to provide a complementarity determining region (CDR)-grafted human antibody which contains at least one CDR from each variable heavy chain and variable light chain of at least one monoclonal antibody, against the RSV antigen. The monoclonal antibody may be derived from any non-human animal, preferably however, it is derived from a rodent and most preferably it is a murine monoclonal antibody. Preferably, the murine monoclonal antibody is a neutralizing antibody. It is also preferable that said murine antibody is an antibody against RSV F antigen.

The term "animal" as used herein is used in its broadest sense includes mammals including humans.

DETAILED DESCRIPTION OF THE DRAWINGS

The drawings depicted and described herein are intended to further illustrate the present invention and are not intended to limit the invention in any manner whatsoever.

FIG. 1A-B shows the amino acid (AA) sequence design of CDR-Grafted anti-RSV F glycoprotein $V_H$. The figure depicts the AA sequence for the human HV3 $V_H$ before grafting (SEQ ID NO:16), CDR grafted $V_H$ (SEQ ID NO:17), and murine MAb1308F $V_H$ (SEQ ID NO:18) from which the CDR sequence was grafted. The heavily underlined regions identify the CDR sequence which was grafted into the human HV3 $V_H$ and each of the three regions is identified as CDR1, CDR2 and CDR3, respectively.

FIG. 2A-B shows the amino acid (AA) sequence design of CDR-Grafted anti-RSV F Protein $V_L$. The figure depicts the AA sequence for the human K102 $V_L$ before grafting (SEQ ID NO:19), CDR grafted $V_L$ (SEQ ID NO:20), and murine MAb1308F $V_L$ (SEQ ID NO:21) from which the CDR sequence was grafted. The heavily underlined regions identify the CDR sequence which was grafted into the human K102 $V_L$ and each of the three regions is identified as CDR1, CDR2 and CDR3, respectively.

FIG. 3A-B depicts the oligonucleotides used to make Hu1308 $V_H$, the sequences which are underlined are the specific primer sequences (SEQ ID NO:22-25).

FIG. 4A-B depicts the oligonucleotides used to make Hu1308 $V_L$, the sequences which are underlined are the specific primer sequences (SEQ ID NO:26-29).

FIG. 7A-B shows the amino acid (AA) sequence design of CDR-Grafted anti-RSV F glycoprotein $V_H$. The figure depicts the AA sequence for the human COR $V_H$ before grafting (SEQ ID NO:30), CDR grafted $V_H$ (SEQ ID NO:31), and murine MAb1129 $V_H$ (SEQ ID NO:32) from which the CDR sequence was grafted. The heavily underlined regions identify the CDR sequence which was grafted into the human COR $V_H$ and each of the three regions is identified as CDR1 (SEQ ID NO:43), CDR2 (SEQ ID NO:44) and CDR3 (SEQ ID NO:45), respectively.

FIG. 8A-B shows the amino acid (AA) sequence design of CDR-Grafted anti-RSV F Protein $V_L$. The figure depicts the AA sequence for the human K102 $V_L$ before grafting (SEQ ID NO:33), CDR grafted $V_L$ (SEQ ID NO:34), and murine MAb1129 $V_L$ (SEQ ID NO:35) from which the CDR sequence was grafted. The heavily underlined regions identify the CDR sequence which was grafted into the human K102 $V_L$ and each of the three regions is identified as CDR1 (SEQ ID NO:46), CDR2 (SEQ ID NO:47) and CDR3 (SEQ ID NO:48), respectively.

FIG. 9A-B shows the oligonucleotides used to construct the humanized 1129 V (SEQ ID NO:36-42).

Figure 10:
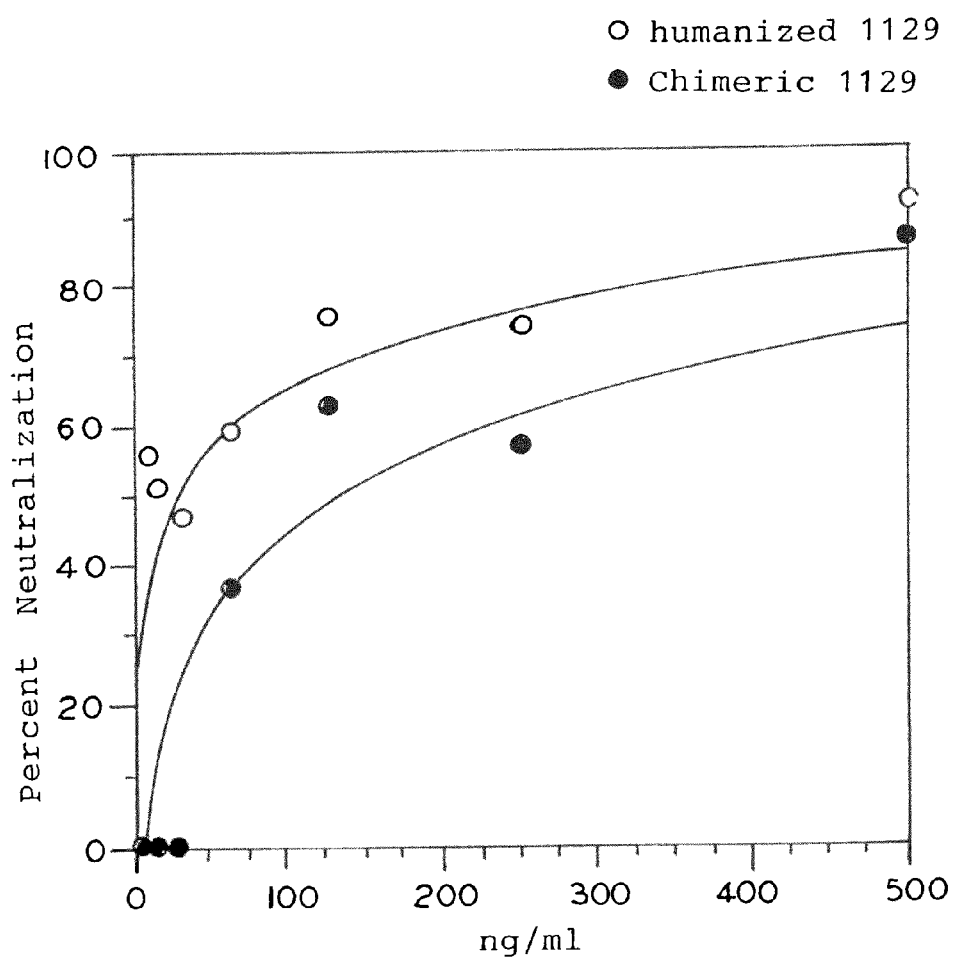

FIG. 10 shows binding data for humanized 1129 in an ELISA assay.

DETAILED DESCRIPTION OF THE INVENTION

Applicants have found that transplantation into a human antibody, of only the genetic information for at least one CDR from each of the variable heavy and variable light chain derived from murine monoclonal antibody against RSV antigen, is effective for the prevention and treatment of RSV in animals. Preferably the murine antibody is a neutralizing antibody against RSV. Another aspect of the present invention provides for the murine antibody to be an antibody against RSV F antigen. Preferably, the murine antibody is neutralizing antibody against RSV F antigen. The substitution of the mouse CDR's into the human variable framework segments minimizes the potential for human anti-mouse antibody (HAMA) responses while retaining binding affinity and specificity for antigen, RSV F protein. Since, the CDR's do not contain characteristic murine or human motifs, the human antibodies containing the murine antibody CDR's are essentially indistinguishable from completely human antibodies, thereby, minimizing the human antibody response while retaining binding affinity and specificity for RSV F antigen.

The development of a humanized antibody against RSV F antigen began with a murine antibody against RSV F antigen. Examples of murine antibodies of this type are: MAb 1436C, MAb 113, MAb 112, MAb 151, MAb 1200, MAb 1214, MAb 1237, MAb 1129, MAb 1121, MAb 1107, MAb 131-1, MAb 43-1, MAb 1112, MAb 1269, MAb 1243, MAb 1331H, MAb 1308F and MAb 1302A (see citation 21).

An aspect of the present invention provides that the CDRs of the human antibody are comprised of three complementarity determining regions (CDRs) from each variable heavy and variable light chain of the murine antibody.

The murine antibodies against RSV F antigen have been mapped by competitive binding and reactivity profiles of virus escape mutants to three broad antigenic sites (A, B, C) containing 16 distinct epitopes (20). The epitopes within antigenic sites A and C have shown the least variability in natural isolates.

Therefore, another aspect of this invention provides for a human antibody containing at least one CDR from each variable heavy and variable light chain of at least one murine antibody against RSV F antigen which is specific for antigenic site A or C. In one aspect, this invention provides for the murine antibody against RSV F antigen specific for antigenic site C, where the murine antibody is MAb 1308F.

In such an embodiment of this invention a human antibody contains CDR's of the variable heavy chain of murine antibody MAb 1308F against the RSV F antigen. The CDR variable heavy chain of MAb 1308F comprises three CDRs having the following amino acid sequences: Nos. 31 to 35, 47 to 60 and 99 to 106. In addition, this embodiment contains CDR's of a variable light chain of MAb 1308F of murine antibody against RSV F antigen. The CDR variable light chain comprises three CDR's having the following amino acid sequences: Nos. 24 to 34, 50 to 56 and 89 to 97.

Another aspect of this invention provides for a human antibody containing at least one CDR from each variable heavy and variable light chain of at least one murine antibody against RSV F antigen which is specific for antigenic site A. Preferably, this invention provides for the murine antibody against RSV F antigen specific for antigenic site A, where the murine antibody is MAb 1129.

In the embodiment of this invention a human antibody which contains CDR's of the variable heavy chain of murine antibody MAb 1129 against the RSV F antigen. The CDR variable heavy chain of MAb 1129 comprises three CDRs having the following amino acid residues: Nos. 31 to 37, 52 to 67 and 100 to 109. In addition, this embodiment contains CDR's of a variable light chain of MAb 1129 of murine antibody against RSV F antigen. The CDR variable light chain comprises three CDR's having the following amino acid residues: Nos. 24 to 33, 50 to 56 and 89 to 97.

An additional aspect of applicants' invention is a process for preventing or treating RSV infection comprising administering to the animal an effective amount of a human antibody containing at least one CDR from each variable heavy and variable light chain, of at least one murine antibody against RSV F antigen.

Another aspect of applicants' invention is a composition comprising administering an effective amount of the human antibody as described above in conjunction with an acceptable pharmaceutical carrier. Acceptable pharmaceutical carriers include but are not limited to non-toxic buffers, fillers, isotonic solutions, etc.

The composition of Applicant's invention may be administered topically or systemically. Examples of topical administration are intranasal administration and inhalation of an aerosol containing the human antibody composition. Systemic administration may be accomplished by intravenous or intramuscular injection of the human antibody composition.

A preferred aspect of Applicants' invention is that the human antibody is administered as part of a plurality of human antibodies against RSV F antigen. These antibodies can be against the same or different epitopes of the RSV F antigen.

Additionally, the human antibody of this invention can be used clinically for diagnosing respiratory syncytial virus in patients. Because of their affinity for RSV F antigen these human antibodies can be used in known diagnostic assay procedures for detecting the presence and concentration of RSV F antigen cells in samples, e.g., body fluids. The human antibodies of the present invention can for example be attached or bound to a solid support, such as latex beads, a column, etc., which are then contacted with a sample believed to contain RSV F antigen.

Applicants' development of human antibodies against RSV, began with murine hybridoma cells producing murine monoclonal antibodies which have been shown to neutralize RSV in vitro and protect cotton rats against lower respiratory tract infection with RSV.

One such antibody was selected, which is specific for antigenic site C, to produce mouse-human chimeric antibodies.

This antibody was chosen on the basis that it: (i) reacted with a large number of virus strains tested (at least 13 out of 14 isolated); (ii) retained neutralizing activity against virus escape mutants selected with other anti-F antibodies and (iii) blocked RSV replication when administered at low doses to cotton rats by intranasal route prior to virus challenge. The antibody showed significant reduction in pulmonary virus titer among antibodies in that respective region. Murine antibody 1308F, specific for the C region of RSV F protein, was chosen as the initial target for humanization.

In summary, the human antibodies were constructed as follows: the RNA was extracted from the murine antibody-producing cell line, the murine variable regions which are responsible for the binding of the antibody to RSV were cloned and sequenced, resulting in the identification of the murine antibody CDRs. Then a human variable heavy and light chain framework sequence having the highest homology with the variable heavy and light chain murine antibody, was selected. A human framework sequence such as described above is best able to accept the murine-derived CDRs.

The murine 1308F variable heavy chain was compared to various human germline genes, the highest homology was to the human germline gene HV3. The two sequences were 62% homologous overall and 65% in the framework regions. Significantly, there is good homology at the junctions of the CDR segments and the frameworks with the exception of the 5' end of FR2. The murine derived variable heavy chain CDRs were then substituted into the variable heavy chain human germline gene HV3. The mouse and human sequences as well as that of a potential CDR-Grafted combination of the two is shown in FIG. 1A-B.

A similar analysis of the $V_L$ region revealed high homology to the human germ line V-Kappa gene K 102. The alignment of these sequences is shown in FIG. 2A-B. In this case the homology is 62% overall and 73% in the framework regions. The murine-derived variable light CDRs were then substituted into the human variable light chain of human germline gene K102. In each case a human J-region can be selected which is identical to the mouse sequence.

In another embodiment, murine 1129 variable heavy chain was compared to various human variable region amino acid sequences, the highest homology was to the human rearranged COR sequence. The two amino acid sequences were 75% homologous overall and 80% in the framework regions. Significantly, there is good homology at the junctions of the CDR segments and the frameworks. The murine derived variable heavy chain CDRs were then substituted into the variable heavy chain human COR $V_H$ sequence. The mouse and human sequences as well as that of a potential CDR-Grafted combination of the two is shown in FIG. 7A-B.

A similar analysis of the $V_L$ region revealed high homology to the human germ line K102. The alignment of these sequences is shown in FIG. 8A-B. In this case the homology is 73% overall and 82% in the framework regions. The murine-derived variable light CDRs were then substituted into the human variable light chain of human germline K102. In this case a human J-region, human JK4, was selected which is similar to the mouse sequence.

Therefore, human antibodies are expressed and characterized relative to the parental murine antibodies to be certain that the genetic manipulation has not drastically altered the binding properties of the antibodies.

Applicants present herein examples which are further illustrative of the claimed invention but not intended to limit the invention.

EXAMPLE 1 cDNA Cloning and Sequencing of Anti-RSV F Protein Antibody 1308F cdNA copies of the $V_H$ and $V_L$ of the target antibody were generated as follows. The first strand cDNA reaction was carried out using AMV reverse transcriptase and a phosphorylated oligonucleotide primer complementary to a segment of the mRNA coding for the constant region of the particular heavy or light chain isotype. For 1308F the isotype is gammal, kappa and the specific oligonucleotides were 5'AGCGGATCCAGGGGCCAGTGGATAGAC (SEQ ID NO:1) complementary to codons 129-137 of the CH1 region of the murine Gammal gene, and 5'TGGATGGTGGGAAGATG (SEQ ID NO:2) complementary to codons 116-122 of the murine C-kappa gene. The primer anneals to a segment of the mRNA adjacent to the variable region. Second strand cDNA synthesis was carried out using RNase H and *E. coli* DNA polymerase I, as described by Gubler and Hoffman (Gene 25; 263, 1983), followed by T4 DNA polymerase to assure that blunt ends are produced.

| Signal | V | J | C | mRNA |
|--------|---|---|---|------|
|        | 1st | strand | cDNA | |
|        | 2nd | strand | cDNA | |

The ds-cDNA was ligated into pUC18 which had been digested with restriction endonuclease SmaI and treated with alkaline phosphatase. The ligation was used to transform *E. coli* DH5a by the method of Hanahan (J. Mol. Biol. 166; 557, 1983). Oligonucleotide probes corresponding to C-region sequence lying between the first strand cDNA primer and the V-region were used in colony hybridizations to identify transformants carrying the desired cDNA segment. The specific probe sequences were GGCCAGTGGATAGAC (SEQ ID NO:3) complementary to codons 121-125 of murine CH1 regions and TACAGTTGGTGCAGCA (SEQ ID NO:4) complementary to codons 110-115 of c-Kappa, respectively. Candidate plasmids, isolated from colonies which were positive in the hybridization, were analyzed by digestion with restriction endonucleases Eco RI and Hind III to release the cDNA insert. Those with inserts of 400-500 bp were subjected to DNA sequencing.

The cDNA inserts were inserted into M13 mp18 and mp19 for the determination of the DNA sequence on both strands. Single stranded DNA from the resulting recombinant bacteriophage was isolated and sequenced by the dideoxy chain termination method (Proc. Nat. Acad. Sci. USA 74; 5463, 1977).

In order to confirm that the pair of rearranged and somatically mutated V gene cDNA's isolated from the 1308F hybridoma represented those which were in the 1308F antibody, a single-chain Fv gene was generated, expressed in and secreted from mammalian cells, then assayed for binding to RS virus. Competition binding experiments then were used to demonstrate the identity of the binding site.

EXAMPLE 2

Design and Assembly of Human 1308F $V_H$ and $V_L$

The CDR regions of the $V_H$ and $V_L$ were identified by comparing the amino acid sequence to known sequences as described by Kabat (38). In order to select the human framework sequences best able to accept the mouse derived CDR sequences in a conformation which retains the structure of the antigen combining site, the following strategy was employed. First, the sequence of the murine $V_H$ and $V_L$ regions will be compared to known human sequences from both the Genbank and NBRF protein databanks using the Wordsearch program in the Wisconsin package of sequence manipulation programs (Nucleic Acid Res. 12; 387). The best several human V-regions were then analyzed further on the basis of similarity in the framework regions, especially at the junctions of the framework and CDR regions (see FIGS. 1A-B and 2A-B).

The CDR-grafted $V_H$ region together with the respective leader sequence of the human v-region gene was synthesized de novo using four overlapping oligonucleotides ranging from 100-137 nucleotides in length (see FIG. 3A-B). The oligonucleotides were first allowed to anneal in pairwise combinations and extended with DNA polymerase to generate approximately 200 bp ds DNA fragments with an overlapping region. the fragments were then mixed and subjected to PCR using primers at the 3' end of one fragment and the 5' end of the other fragment. The only product which can be formed under these condition is the full length $V_H$ segment. The specific primer sequences are underlined in FIG. 3A-B. An endonuclease Sac I site was included at the 3' end of the $V_H$ sequence in order to join it to a human constant region gene segment.

The CDR-grafted $V_L$ region was synthesized in a similar way (see FIG. 4A-B). In this instance the initial 200 bp fragments were amplified separately and inserted into separate plasmids. The fragment coding for the amino terminus was cloned into a pUC18 derivative as an NcoI-SmaI fragment while the fragment coding for the carboxyl-terminus was cloned as a SmaI to Hind III fragment. The fragments were subsequently combined via a SmaI site at the junction. The oligonucleotides are indicated in FIG. 4A-B. A Hind III site was included near the 3' end of the gene segment in order to join it to a human C-kappa gene.

EXAMPLE 3

Construction of Vectors for 1308F Expression

The NcoI-SacI fragment representing the humanized $V_H$ was joined to a SacI-NotI fragment representing a human c-Gamma I cDNA and inserted into pS 18 (which is pUC18 with NcoI and NotI restriction sites incorporated into the polylinker region between the BamHI and Kpn1 sites). The humanized 1308F-gammaI gene on a SacI-NotI fragment was then combined with a PvuI-NotI fragment from pSJ37 carrying a poly A addition site and a PvuI-SacI fragment from pSV2-dhfr-pCMV containing the SV40 origin of replication, a dhfr gene and the CMV immediate early promoter. The resulting plasmid was designated pSJ60.

The NcoI-HindIII fragment representing the humanized $V_L$ was joined to a HindIII-NotI fragment representing a human c-Kappa cDNA in pS18. The humanized 1308F-Kappa gene on a SalI-NotI fragment was then combined with a PvuI-NotI fragment from pSJ37 carrying a poly A addition site and a PvuI-SalI fragment from pSV2-dhfr-pCMV, containing the SV40 origin of replication, a dhfr gene and the CMV immediate early promoter. The resulting plasmid was designated pSJ61.

Figure 5:
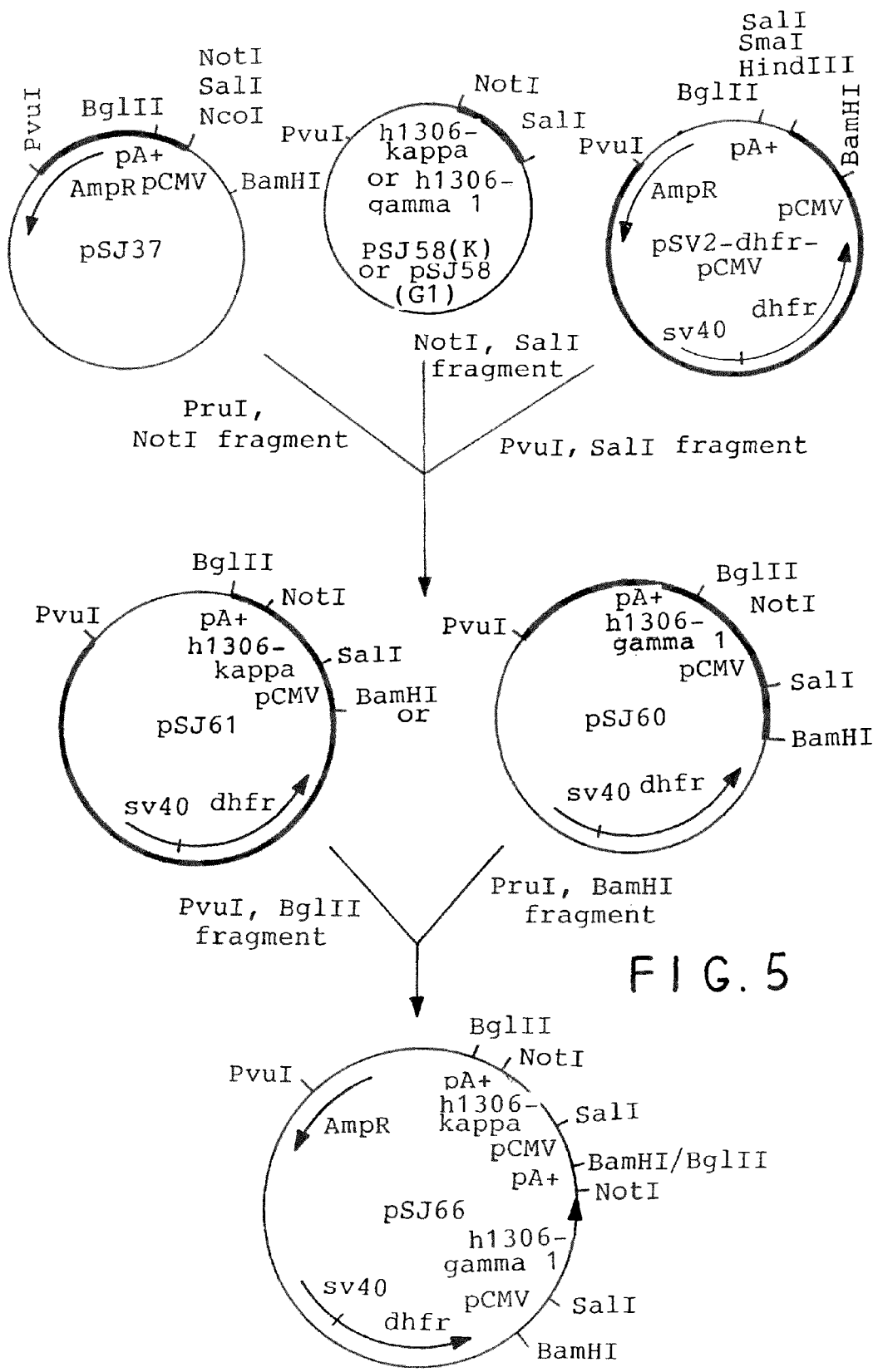
FIG. 5 depicts the plasmid construction of the expression vectors for Humanized 1308.

Finally pSJ60 and pSJ61 were combined into a single plasmid containing both the light and heavy chains and expression signals. This was accomplished by isolating a PvuI-Bam HI fragment from pSJ61 carrying the light chain with a PvuI-Bgl II fragment from pSJ60 carrying the heavy chain to generate pSJ66. (See FIG. 5).

EXAMPLE 4

Transfection of Cosl Cells with PSJ60 and PSJ61

Transfections were carried out according to the method of McCutchan and Pagano (J. Nat. Can. Inst. 41: 351-356, 1968) with the following modifications. COS1 cells (ATCC CRL1650) were maintained in a humidified 5% $CO_2$ incubator in 75 $cm^2$ tissue culture flasks in Dulbecco's Modified Eagle Medium (DMEM, GIBCO #320-1965) supplemented with 10% Fetal Bovine Serum (FBS, GIBCO #200-6140) and 2 mM L-glutamine (BRL #320-5030) and passed at a split ratio of 1:20 when the cells had reached confluence. 48 hours prior to transfection, 5 100 mm tissue culture dishes were seeded with $1.5 \times 10^6$ cells per dish in 12 ml DMEM, 10% FBS, 2 mM L-glutamine, 1% penicillin-streptomycin (P-S, GIBCO #600-5070). The day of the transfection, 120 ug each of the plasmids pSJ60 and pSJ61 were combined, ethanol precipitated, and aseptically resuspended in 2.5 ml Tris-Buffered-Saline. The resuspended DNA was added dropwise, with mixing, to 10 ml of DMLEM containing 1 mg/ml DEAE-dextran (Phamiacia #17-0350-01) and 250 uM chloroquine (Sigma #C6628). The medium was removed from the COS1 cells in the 100 mm dishes and the cells were washed once with Dulbecco's phosphate buffered saline (D-PBS, GIBCO #310-4190), and 2.5 ml DMEM supplemented with 10% NuSerum (Collaborative Research #55000) were added to each plate. 2.5 ml of the DNA/DEAE-dextran/chloroquine mix were added dropwise to each plate, the plates swirled to mix the DNA, and were returned to the incubator. After 4 hours in the incubator, the supernatant was aspirated from the cells and the cells were washed once with 5 ml D-PBS. The cells were shocked for 3 minutes by the addition of 5 ml of 10% dimethylsulfoxide (DMSO) in D-PBS at room temperature. The DMSO was aspirated from the cells and the cells were washed with 5 ml D-PBS. 14 ml of DMEM/10% FBS/2 mM L-glutamine/1% P-S were added to each plate and the plates were returned to the incubator.

Three days post-transfection the medium was removed from the plates, pooled, and stored at −20 C. The cells were harvested, pooled, and seeded into 4 150 $cm^2$ tissue culture flasks two with 40 ml DMEM/10% NuSerum and two with 40 ml DMEM/10% FBS/2 mM L-glutamine. The medium was collected and the cells refed at 7, 10, and 14 days. In this way a total of 125 ug of humanized 1308F antibody was accumulated in 310 ml of medium supplemented with FBS and 85 ug in 240 ml of medium supplemented with NuSerum.

EXAMPLE 5

Transfections of COS1 Cells with PSJ66

48 hours prior to transfection, 5 100 mm tissue culture dishes were seeded with $1.5 \times 10^6$ cells per dish in 12 ml DMEM, 10% FBS, 2 mM L-glutamine, 1% penicillin-streptomycin (P-S, GIBCO #600-5070). The day of the transfection, 125 ug of the plasmid pSJ66 were ethanol precipitated and aseptically resuspended in 1.0 ml Tris-Buffered-Saline. The resuspended DNA was added dropwise, with mixing, to 4.0 ml of DMEM containing 1 mg/ml DEAE-dextran (Pharmacia #17-0350-01) and 250 uM chloroquine (Sigma #C6628). The medium was removed from the COS1 cells in the 100 mm dishes and the cells were washed once with Dulbecco's phosphate buffered saline (D-PBS, GIBCO #310-4190), and 2.5 ml DMEM supplemented with 10% NuSerum (Collaborative Research #55000) were added to each plate. 2.5 ml of the DNA/DEAE-dextran/chloroquine mix were added dropwise to each plate, the plates swirled to mix the DNA, and were returned to the incubator. After 4 hours in the incubator, the supernatant was aspirated from the cells and the cells were washed once with 5 ml D-PBS. The cells were shocked for 3 minutes by the addition of 5 ml of 10% dimethylsulfoxide (DMSO) in D-PBS at room temperature. The DMSO was aspirated from the cells and the cells were washed with 5 ml D-PBS. 14 ml of DMEM/10% FBS/2 mM L-glutamine/1% P-S were added to each plate and the plates were returned to the incubator.

Three days post-transfection the medium was removed from the plates, pooled, and stored at −20 C. The cells were harvested, pooled, and seeded into 4 150 cm.sup.2 tissue culture flasks two with 40 ml DMEM/10% NuSerum and two with 40 ml DMEM/10% FBS/2 mM L-glutamine. The medium was collected and the cells refed at 7, 10, and 14 days. In this way a total of 190 ug of humanized 1308F antibody was accumulated in 310 ml of medium supplemented with FBS and 120 ug in 240 ml of medium supplemented with NuSerum.

The concentration of humanized 1308F antibody secreted from the Cos1 cells into the medium was determined using a capture ELISA. Goat anti-human IgG Fc coated onto 96 well plates was used to capture the humanized antibody. Peroxidase conjugated goat anti-human whole IgG developed with a chromogenic substrate was then used to detect the bound antibody. A purified human IgG1/Kappa preparation was used to calibrate the assay.

EXAMPLE 6

Neutralization of RSV with Humanized 1308F

Figure 6:
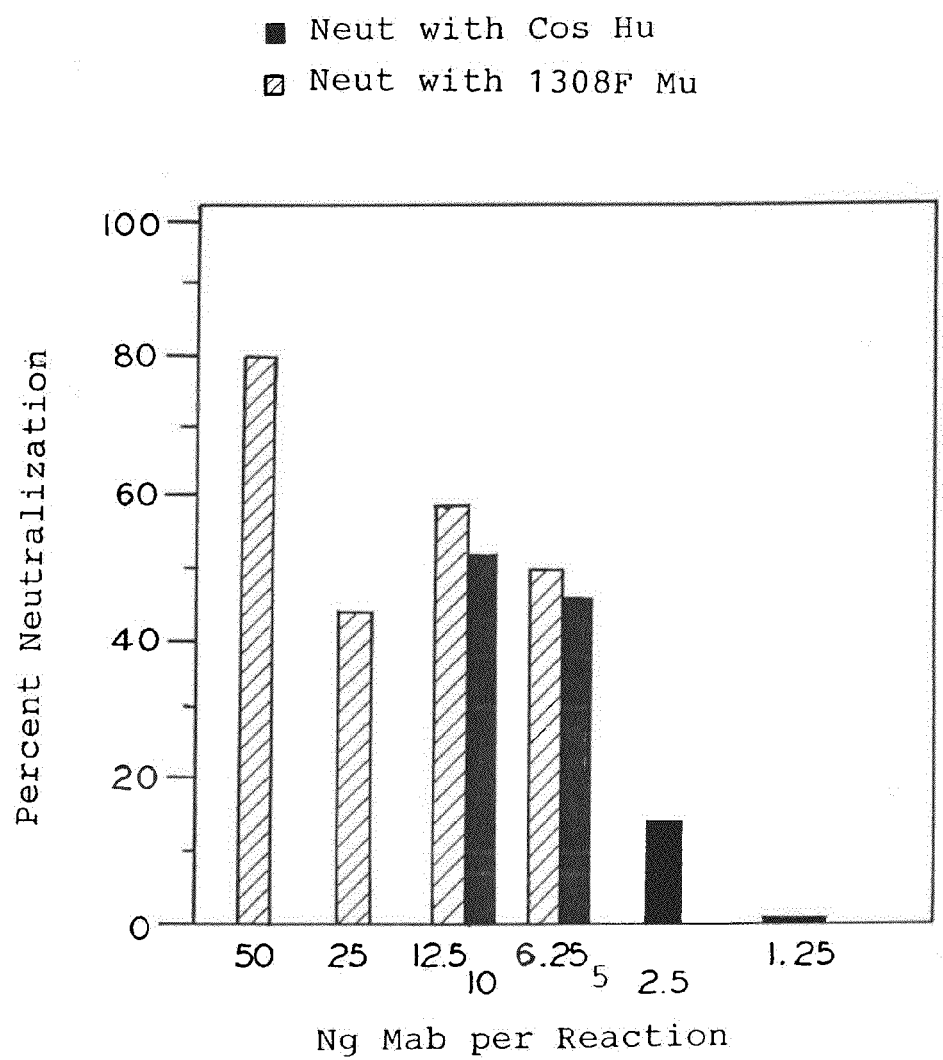
FIG. 6 depicts a graph of the neutralization of RSV as percent neutralization versus ng MAb per reaction for neutralizing with Cos Hu1308F and with Mu1308F.

Methods:

RSV was neutralized with either humanized 1308F from Cos cell supernatant or purified 1308F murine monoclonal antibody. This was done by incubating 50 plaque-forming units of RSV with serial 2-fold dilutions of antibody for 1.0 hour at 37 C. Confluent monolayers of Hep2 cells in 24 well panels were infected with 100 µl of antibody treated virus, untreated control virus, and mock infected controls. Incubated for 1.5 hours at 37 C, humidified, tand 5% $CO_2$ and overlayed with 1.5 mL EMEM, 1% FBS, and 1% methyl cellulose. Cells were fixed and stained with glutaldehyde and crystal violet on day 4. Plaques were counted in triplicate wells and plotted as percent neutralization. The results shown in FIG. 6 indicate that both the purified murine 1308F monoclonal and the humanized 1308F monoclonal antibody at 5 to 10 ng per well yield similar 50% reductions in RSV plaques.

EXAMPLE 7

Generation of a CDR-Grafted A-Site Antibody 1129

Poly-A+ RNA was purified from a lysate of $2\times10^7$ murine 1129 hybridoma cells using oligo-dt cellulose. First strand cDNA was made from 1 ug pA+ RNA using random hexamer primers and AMV reverse transcriptase 1 ug pA+ RNA, 50 mM Tris-HCl pH 8.5, 8 mM $Mg_2Cl$, 30 mM KCl, 1 mM dithiothrietol, 1 mM dNTP's, 25 units of placental ribonuclease inhibitor, 33 uM random hexamer and 10 units of AMV reverse transcriptase for one hour at 42° C. The cDNA from the 1129 VL region was amplified by PCR using oligonucleotides SJ41 and SJ11, see Table 1. cDNA from the 1129 VH region was similarly amplified using oligonucleotides SJ42 and SJ10, see Table 1.

TABLE 1

| Oligonucleotide | Sequence | SEQ ID NO. |
|---|---|---|
| SJ10 | AGCGGATCCAGGGGCCAGTGGATAGAC | 1 |
| SJ11 | GATGGATCCAGTTGGTGCAGCATC | 5 |
| SJ41 | CACGTCGACATTCAGCTGACCCAGTCTCCA | 6 |
| SJ42 | CGGAATTCAGGTIIAICTGCAGIAGTC(A,T)GG (I = deoxy-Inosine) | 7 |
| SJ53 | CCCAAGCTTGGTCCCCCCTCCGAACGTG | 8 |
| SJ154 | GGCGTCGACTCACCATGGACATGAGGGTCC(C/T)CGCTCAGC | 9 |
| SJ155 (H1129L CDR 1) | GTCACCATCACTTGCAAGTGCCAGCTGAGTGTAGGTTACATGCACTGGTACCAGCAG | 10 |
| SJ157 (H1129L CDR 3) | GCAACTTATTACTGCTTTCAGGGGAGTGGGTACCCATTCACGTTCGGAGGGGGG | 11 |
| SJ168 | GTGACCAACATGGACCCTGCTGATACTGCCAC | 12 |
| SJ169 | CCATGTTGGTCACTTTAAGGACCACCTGG | 13 |
| SJ170 | CCAGTTTACTAGTGTCATAGATCAGGAGCTTAGGGGC | 14 |
| SJ171 | TGACACTAGTAAACTGGCTTCTGGGGTCCCATCAAGG | 15 |

PCR Conditions:

0.5 uL of 1st strand cDNA, 10 mM Tris-HCl pH8.3, 50 mM KCl, 1.5 mM $Mg_2Cl$, 0.2 mM dNTP's, 0.001% gelatin, 1 uM each primer, 1 ng DNA template and 2.5 u AmpliTaq™ DNA polymerase (Perkin Elmer-Cetus). 94° 1 minute, 55° 2 minutes, 72° 2 minutes in Perkin Elmer 480 thermocycler for 25 cycles. The resulting DNA fragment(s) were then extracted once with phenol/chloroform (1/1), precipitated with 2.5 volumes of ETOH, resuspended in the appropriate restriction endonuclease buffer and digested with restriction endonucleases to produce cohesive ends for cloning. The resulting fragments were then separated by electrophoresis on a 1% agarose gel. After staining the gel with ethidium bromide the fragments were excised and purified from the agarose by freezing and extraction in the presence of phenol.

The fragments were then digested with restriction endonucleases EcoR1 and BamH1 and cloned into plasmid pUC18. The inserts were then sequenced by the dideoxynucleotide chain termination method using modified T7 DNA polymerase (Seqeunase, US Biochemical). The translated sequences were compared to human antibody protein sequences. The VL was found to be most homologous to the K102 light chain and the VH was found to be most homologous to the Cor VH region. The 1129 Fv region was then modeled by substitution of the residues from the 1129 VL and VH sequence into the coordinates of corresponding residues in the crystal structure the MCPC603 antibody. Residues were identified as being integral to the folded structure or solvent exposed by visual inspection of the model.

Several residues which were integral and which were different in the mouse and human sequences were left as the mouse residue in order to maintain the integrity of the Fv and thus the binding site. Such residues were 31, 83, 113, and 116 on the VH and 47 in the VL region. The resulting sequences are shown in FIGS. 7A-B and 8A-B.

The designed humanized 1129 VH was constructed using synthetic oligonucleotides SJ147-SJ153 (FIG. 9A-B) (SEQ ID NO:36-42) which were combined using PCR. The products of this PCR were then digested with Nco1 and Sac1 and cloned into plasmid vector pSJ40 which is a pUC18 derivative in which an out of frame lacZ1 segment is restored in frame as a fusion to an in-frame V region segment when such a segment is inserted as an Nco1-Sac1 fragment. A plasmid containing an insert in which 5 mutations were clustered in a single 50 bp region was then subjected to repair of these changes using recombinant PCR and the primers SJ168 and SJ169, see Table 1.

The VL was generated by site directed mutagenesis of the humanized 1308F light chain gene. Oligonucleotides SJ155, see Table 1, (CDR1), and SJ157 (CDR3) were used to separately mutagenize the H1308L gene. Mutagenesis was carried out using T7 DNA polymerase on uracil containing single stranded DNA templates generated in E. coli strain BW313 (dut-,ung-) and subsequently transformed into E. coli strain DH5 (dut+,ung+). The two mutants were combined and CDR2 introduced by recombinant PCR using oligonucleotides SJ170, SJ154, see Table 1, (5' end) and SJ171, SJ53, see Table 1, (3' end). The CDR-grafted VH and VL genes were placed into pSJ60 (see Example 3) and pSJ61 (see Example 3), respectively as Nco1-Sac1 fragments in place of the H1308F V region segments resulting in plasmids pSJ81 and pSJ105. In addition the murine VH and VL cDNA segments were similarly joined to human C-Gammal and CKappa respectively to generate expression vectors pSJ75 and pSJ84.

EXAMPLE 8

Hu1129 Transient Expression

COS1 cells (ATCC CRL1650) were maintained in a humidified 5% $CO_2$ incubator in 75 $cm^2$ tissue culture flasks in Dulbecco's Modified Eagle Medium (DMEM, GIBCO #320-1965) supplemented with 10% fetal bovine serum (FBS, GIBCO #200-6140) and 2 mM L-glutamine (GIBCO #320-5030) and passed at a split ratio of 1:20 just prior to reaching confluence.

Transfections were carried out according to the method of McCutchan and Pagano (J. Nat. Can. Inst. 41: 351-356, 1968) with the following modifications. Twenty four hours prior to transfection 100 mm tissue culture dishes (Corning #25020) were seeded with $2 \times 10^6$ COS1 cells per dish in 14 ml DMEM, 10% FBS, 2 mM L-glutamine. The day of the transfection 10 ug of the Hu1129 heavy chain plasmid (pSJ81, from Example 7 were combined with 10 ug of the Hu1129 kappa light chain plasmid pSJ105, from Example 7, the DNA was ethanol precipitated and aseptically resuspended in 1.0 ml Tris-Buffered-Saline. The resuspended DNA was added dropwise, with mixing, to 4.0 ml of DMEM containing 1 mg/ml DEAE-dextran (Pharmacia #170350-01) and 250 uM Chloroquine (Sigma #C6628). The medium was removed from the COS1 cell dishes, the cell monolayers were washed once with 10 ml Dulbecco's phosphate buffered saline (D-PBS, GIBCO #310-4190), and 2.5 ml DMEM supplemented with 10% NuSerum (Collaborative Research #55000) and 2 mM L-glutamine were added to each plate. 2.5 ml of the DNA/DEAE dextran/chloroquine mix were added dropwise to each plate, the plates were swirled to mix the DNA, and returned to the incubator. After an eight hour DNA adsorption period the plates were removed from the incubator and the supernatant was aspirated from the plates. The cells were shocked by the addition of 5 ml of 10% DMSO in D-PBS per plate for 3 minutes at room temperature, after which the DMSO was aspirated from the cells and the cells were washed once with 5 ml D-PBS. 15 ml DMEM, 10% NuSerum, 2 mM L-glutamine (production medium) were added to each plate and the plates were returned to the incubator.

Seventy two hours post-transfection the conditioned medium was harvested from the plates and stored at −20° C., and 15 ml production medium was added to the plates and the plates were returned to the incubator. Ninety six hours later the medium was collected from the plates and stored at 20° C.

EXAMPLE 9

Quantitation of Hu1129

Quantitation of the Hu1129 IgG1 antibody secreted into the medium by the COS1 cells was performed using a sandwich type ELISA. In brief, Nunc Maxisorp Immunoplates (Nunc #439454) were coated with 50 ul/well of 0.5 ug/ml goat anti-human IgG Fc (Cappel #55071) in 0.1M sodium bicarbonate pH 9.6 for 3 hours at room temperature. The wells were washed three times with 0.01M sodium phosphate pH 7.4, 0.15M NaCl, 0.1% Tween 20 (PBS-T). Nonspecific protein binding to the plate was blocked by treatment of the wells with 200 ul/well of 3% (w/v) nonfat dry milk in PBS for 30 minutes at room temperature. A purified human IgG1 kappa standard (Sigma #1-3889) was made up at 100 ng/ml in PBS-T and serially diluted 1:2 to 1.56 ng/ml, and 50 ul of each were added to duplicate wells of the assay plate. COS1 cell supernatants were diluted in PBS-T and duplicate 50 ul samples were added to the plate. After an one hour room temperature incubation the wells were evacuated and washed three times with PBS-T. To detect the presence of bound Hu1129 antibody, horseradish peroxidase conjugated affinity purified goat anti-human IgG (whole molecule, Cappel #3601-0081) was diluted 1:1000 in PBS-T and 50 ul was added to each well of the assay plate and incubated at room temperature for one hour. The plate was washed three times with PBS-T and 100 ul of the chromogenic substrate TMBlue (TSI #TM102) was added to each well. The plate was incubated at room temperature in the dark for ten minutes and the reaction was stopped by the addition of 50 ul per well of 4.5M $H_2SO_4$. The plate was read at 450 nm using a Molecular Devices Vmax microplate reader, and data analysis was performed using Softmax software (Molecular Devices) running on an IBM P/S2 model 80 computer.

During the first seventy two hours of production the COS1 cells produced 0.06 ug/ml Hu1129, for a total of 0.9 ug. In the next ninety six hours of production the COS1 cells produced 0.99 ug/ml Hu1129, for a total of 14.85 ug.

EXAMPLE 10

Hu1129 Binding Assay

Binding assays of the Hu1129 were performed in a capture ELISA, essentially as for the quantitation ELISA, but with the following changes. Plates were coated with the Mul 331 antibody at 0.5 ug/well, the wells were blocked with 3% non-fat milk in PBS-T, and 50 ul of RSV infected HEP2 cell lysate was added to each well and incubated at room temperature for 1 hour. The remainder of the assay was carried out as for the quantitation assay starting with the addition of diluted samples to the wells. Results were analyzed as a double reciprocal plot of OD vs antibody concentration from which an apparent Kd for the H1129 molecule of 0.7 nM was determined compared to 10 nM for the M1129 HuGammal, Kappa antibody.

RSV neutralization assays on H1129 and ch1129 antibody were performed according to the following procedure:
1. Unwrap 96 well Costar cell culture plates in hood.
2. Warm Growth Medium (GM) to 37° C.
3. Thaw MA104 cells at 37° C. Dilute to about 150,000 cells per mL with GM. Mix cells and dispense 200 ul per well.
4. Culture cells 37° C., 5% $CO_2$, and humidified overnight before infection.
5. Dilute RSV Stock to 10,000 pfu per mL in Maintenance Medium (MM).
6. Mix equal volume of Antibody diluted in MM with equal volume of diluted RSV. Incubate at 37° C., 5% $CO_2$, and humidified for 1.0 h before infection.
7. Infect replicate wells of MA104 cells with 200 ul of the Antibody and Virus mixture. Infect replicate wells with virus and mock infected controls.
8. Wrap the plates in cellophane and incubate at 37° C., 95% humidity, and 5% $CO_2$ for 5 days.
9. ELISA for RSV: Aspirate each well; add 100 ul 80% Acetone/PBS (vol./vol.) and incubate at room temperature 30 minutes.
10. Aspirate each well and air dry for 30 minutes on the grill of a laminar flow hood.
11. Wash 4 times with PBS, 0.05% Tween 20.
12. Add 100. mu.l of monoclonal antibody to RSV F-protein to each well. Incubate for 1.0 h at 37° C.
13. Wash 4 times with PBS, 0.05% Tween 20.
14. Add 100 ul of anti-murine antibody goat serum-horseradish peroxidase conjugate to each well. Incubate for 1.0 h at 37° C.
15. Wash 4 times with PBS, 0.05% Tween 20.
16. Add 100 ul of a freshly prepared 1:1 mixture of ABTS and peroxide to each well. Incubate at room temperature until the optical density (405 nm) of the virus control is 5 to 10 times that of the mock infected controls.

APPENDIX

Growth Medium (GM):
Minimum Essential Medium (Eagle) with Earle's BSS,
2 mM glutamine,
Eagle's non-essential amino acids 0.1 mM final,
Fetal bovine serum 10% (v/v),
Penicillin 50 units/ml,
Streptomycin 50 mcg/ml
Maintenance Medium (MM): as above with serum reduced to 1 to 2%.
MA104 cell stocks are grown up in T150 flasks with Growth Medium. Stocks are frozen at $3 \times 10^6$ cells per 1.8 mL vial in 10% DMSO and Growth Medium. Stored in a $LN_2$ refrigerator.
RSV stocks: are grown up in MA104 (monkey kidney) or Hep 2 cells in T150 flasks. Add about 0.2 ml (about 100,000 pfu) virus stock per confluent T150. Adsorption for 1.0 h at room temperature. Then add 20 mL maintenance medium with 1% fetal bovine serum. Incubate 4-5 days at 37° C. Collect cells just before 100% cpe by scraping. Spin down cells; remove all but 10 mL of supernatant. Freeze (dry ice-ethanol bath) thaw cell pellet, vortex, re-freeze, and store virus stock in $LN_2$ refrigerator.
ELISA Antibody Buffer: PBS, 0.05% Tween 20 (w/v), 2.0% goat serum (v/v) and 0.5% gelatin (w/v).
RSV F Protein Antibody: Chemicon Mab 858-1 anti-RSV fusion protein diluted about 1:5000 in ELISA Antibody Buffer.
Anti-Murine Serum: Fisher horseradish peroxidase conjugated to goat anti-mouse IgG (Heavy Chain Specific) diluted about 1:4000 in ELISA Antibody Buffer.

The results are shown in FIG. 10, and indicate 25 ng/ml achieved 50% neutralization in this assay while 45 ug/ml of the ch1129 antibody was required for 50% neutralization in this experiment. Over a series of 6 separate assays the mean 50% neutralization value for H1129 was 17 ng/ml. As a control and to compare potency we also assayed a polyclonal human IgG preparation made from the plasma of individuals with high neutralizing titers for RSV. This preparation, termed RSVig (lot #4), gave a mean 50% neutralization value of 2.3 ug/ml over 3 experiments. Thus the H1129 is 100-fold more potent in this assay as the enriched polyclonal preparation.

EXAMPLE 11

Kinetic Analysis of Humanized RSV Mabs by BIAcore™

The kinetics of interaction between humanized RSV Mabs and the RSV F protein was studied by surface plasmon resonance using a Pharmacia BIAcore™ biosensor. A recombinant baculovirus expressing a C-terminal truncated F protein provided an abundant source of antigen for kinetic studies. The supernatant, which contained the secreted F protein, was enriched approximately 20-fold by successive chromatography on concanalvalin A and Q-sepharose columns. The pooled fractions were dialyzed against 10 mM sodium citrate (pH 5.5), and concentrated to approximately 0.1 mg/ml. An aliquot of the F-protein (100 ml) was amine-coupled to the BIAcore sensor chip. The amount immobilized gave approximately 2000 response units (Rmax) Of signal when saturated with either H1129 or H1308F. This indicated that there was an equal number of "A" and "C" antigenic sites on the F-protein preparation following the coupling procedure. Two unrelated irrelevant Mabs (RVFV 4D4 and CMV H758) showed no interaction with the immobilized F protein. A typical kinetic study involved the injection of 35 ml of Mab at varying concentrations (25-300 nM) in PBS buffer containing 0.05% Tween-20 (PBS/Tween). The flow rate was maintained at 5 ml/min, giving a 7 min binding phase. Following the injection of Mab, the flow was exchanged with PBS/Tween buffer for 30 min for determining the rate of dissociation. The sensor chip was regenerated between cycles with a 2 min pulse of 10 mM HCl. The regeneration step caused a minimal loss of binding capacity of the immobilized F-protein (4% loss per cycle). This small decrease did not change the calculated values of the rate constants for binding and dissociation.

The affinity of the various Mabs for binding to the F protein was calculated from the ratio of the first order rate constant for dissociation to the second order rate constant for binding ($Kd=k_{diss}/k_{assoc}$). The value for $k_{assoc}$ was calculated based on the following rate equation:

$$dR/dt = k_{assoc}[\text{Mab}]R\text{max} - (k_{assoc}[\text{Mab}] + k_{diss})R \quad (1)$$

where R and Rmax are the response units at time t and infinity, respectively. A plot of dr/dt as a function of R gives a slope of ($k_{assoc}$ [Mab]+$k_{diss}$)—Since these slopes are linearly related to the [Mab], the value $k_{assoc}$ can be derived from a replot of the slopes versus [Mab]. The slope of the new line is equal to $k_{assoc}$. Although the value of $k_{diss}$ can be extrapolated from the Y-intercept, a more accurate value was determined by direct measurement of $k_{diss}$. Following the injection phase of the Mab, PBS/Tween buffer flows across the sensor chip. From this point, [Mab]=0. Equation (1) thus reduces to:

$$dr/dt = k_{dissr} \text{ or } dR/R = k_{diss}dt \quad (2)$$

Integration of equation (2) gives:

$$\ln(R_0/R_t) = k_{diss}t \quad (3)$$

where $R_0/R_t$) are the response units at time 0 (start of dissociation phase) and t, respectively. Lastly, plotting $\ln(R_0/R_t)$ as a function of t gives a slope of $k_{diss}$.

| Kinetic Constants for RSV Mabs | | | | |
|---|---|---|---|---|
| Mab | $k_a$ (assoc) $M^{-1}sec^{-1}$ | $k_d$(dissoc) $sec^{-1}$ | $t_{1/2}$# (hours) | $Kd(k_d/k_a)$ nM |
| CH1129 | $5.0 \times 10^4$ | $7.5 \times 10^{-5}$ | 2.6 | 1.5 |
| H1129 | $4.9 \times 10^4$ | $6.9 \times 10^{-5}$ | 2.8 | 1.4 |
| M1129 | $3.5 \times 10^4$ | $4.0 \times 10^{-4}$ | 0.48 | 11.4 |
| M1308F | $3.5 \times 10^4$ | $3.8 \times 10^{-5}$ | 5.1 | 1.1 |
| H1308F | $2.2 \times 10^4$ | $5.5 \times 10^{-5}$ | 3.5 | 2.5 |

REFERENCES

1. Hall, C. B., Doiuglas, R. G., Geiman, J. M. et al., N. Engl. J. Med. 293:1343, 1975.
2. Hall, C. B., McBride, J. T., Walsh, E. E. et al., N. Engl. J. Med. 308:1443, 1983.
3. Hall, C. B., McBride, J. T., Gala, C. L. et al., JAMA 254:3047, 1985.
4. Wald, E. R., et al., J. Pediat. 112:154, 1988.
5. Kapikian, A. Z., Mithcell, R. H., Chanock, R. M. et al., Am. J. Epidemiol. 89:405, 1969.
6. Prince, G. A., Hemming, V. G., Horswood, R. L. et al., Virus Res. 3:193, 1985.
7. Hemming, V. G., Prince, G. A., Horswood, R. L. et al., J. Infect. Dis. 152:1083, 1985.
8. Wright, P. F., Belshe, R. B., et al., Infect. Immun. 37:397, 1982.
9. Conrad, D. A., Christenson, J. C., et al., Peditr. Infect. Dis. J. 6:152, 1987.
10. LoBuglio, A. F., Wheeler, R. L., Trang, J. et al., Proc. Natl. Acad. Sci. 86:4220, 1989.
11. Steplewski, Z., Sun, L. K., Shearman, C. W. et al., Proc. Natl. Acad. Sci. 85:4852, 1988.
12. Boulianne, G. L., Hozumi, N., Shulman, M. J. Nature. 312:643, 1984.
13. Sun, L. K., Curtis, P., Rakowicz-Szulczynska, E. et al., Proc. Natl. Acad. Sci. 84:214, 1987.
14. Liu, A. Y., Mack, P. W., Champion, C. I., Robinson, R. R., Gene 54:33, 1987.
15. Morrison, S. L., Johnson, M. J., Hersenber, L. A., Oi, V. T. Proc. Natl. Acad. Sci. 81:6851, 1984.
16. Morrison, S. L. Science 229:1202, 1985.
17. Sahagan, B. G., Dorai, H., Saltzgaber-Muller, J. et al., J. Immunol. 137:1066, 1986.
18. Taked, S., Naito, T., Hama, K., Noma, T., Honjo, T., Nature 314:452, 1985.
19. Carson, D. A., Freimark, B. D., Adv. Immunol. 38:275, 1986.
20. Beeler, J. A., et al., J. Virol. 63:2941-2950, 1989.
21. Coelingh, et al., Virology, 143:569-582, 1985.

SEQUENCE LISTING

<160> NUMBER OF SEQ ID NOS: 49

<210> SEQ ID NO 1
<211> LENGTH: 27
<212> TYPE: DNA
<213> ORGANISM: Homo sapiens

<400> SEQUENCE: 1
agcggatcca ggggccagtg gatagac                                    27

<210> SEQ ID NO 2
<211> LENGTH: 17

```
<212> TYPE: DNA
<213> ORGANISM: Homo sapiens

<400> SEQUENCE: 2
tggatggtgg gaagatg                                                      17

<210> SEQ ID NO 3
<211> LENGTH: 15
<212> TYPE: DNA
<213> ORGANISM: Homo sapiens

<400> SEQUENCE: 3
ggccagtgga tagac                                                        15

<210> SEQ ID NO 4
<211> LENGTH: 16
<212> TYPE: DNA
<213> ORGANISM: Homo sapiens

<400> SEQUENCE: 4
tacagttggt gcagca                                                       16

<210> SEQ ID NO 5
<211> LENGTH: 24
<212> TYPE: DNA
<213> ORGANISM: Homo sapiens

<400> SEQUENCE: 5
gatggatcca gttggtgcag catc                                              24

<210> SEQ ID NO 6
<211> LENGTH: 30
<212> TYPE: DNA
<213> ORGANISM: Homo sapiens

<400> SEQUENCE: 6
cacgtcgaca ttcagctgac ccagtctcca                                        30

<210> SEQ ID NO 7
<211> LENGTH: 30
<212> TYPE: DNA
<213> ORGANISM: Homo sapiens
<220> FEATURE:
<221> NAME/KEY: misc_feature
<222> LOCATION: (13)..(14)
<223> OTHER INFORMATION: n is a, c, g, or t
<220> FEATURE:
<221> NAME/KEY: misc_feature
<222> LOCATION: (16)..(16)
<223> OTHER INFORMATION: n is a, c, g, or t
<220> FEATURE:
<221> NAME/KEY: misc_feature
<222> LOCATION: (23)..(23)
<223> OTHER INFORMATION: n is a, c, g, or t

<400> SEQUENCE: 7
cggaattcag ctnnanctgc agnagtcwgg                                        30

<210> SEQ ID NO 8
<211> LENGTH: 28
<212> TYPE: DNA
<213> ORGANISM: Homo sapiens

<400> SEQUENCE: 8
cccaagcttg gtccccctc cgaacgtg                                           28
```

-continued

<210> SEQ ID NO 9
<211> LENGTH: 39
<212> TYPE: DNA
<213> ORGANISM: Homo sapiens

<400> SEQUENCE: 9
ggcgtcgact caccatggac atgagggtcc ycgctcagc                    39

<210> SEQ ID NO 10
<211> LENGTH: 57
<212> TYPE: DNA
<213> ORGANISM: Homo sapiens

<400> SEQUENCE: 10
gtcaccatca cttgcaagtg ccagctgagt gtaggttaca tgcactggta ccagcag    57

<210> SEQ ID NO 11
<211> LENGTH: 54
<212> TYPE: DNA
<213> ORGANISM: Homo sapiens

<400> SEQUENCE: 11
gcaacttatt actgctttca ggggagtggg tacccattca cgttcggagg gggg       54

<210> SEQ ID NO 12
<211> LENGTH: 32
<212> TYPE: DNA
<213> ORGANISM: Homo sapiens

<400> SEQUENCE: 12
gtgaccaaca tggaccctgc tgatactgcc ac                           32

<210> SEQ ID NO 13
<211> LENGTH: 29
<212> TYPE: DNA
<213> ORGANISM: Homo sapiens

<400> SEQUENCE: 13
ccatgttggt cactttaagg accacctgg                               29

<210> SEQ ID NO 14
<211> LENGTH: 37
<212> TYPE: DNA
<213> ORGANISM: Homo sapiens

<400> SEQUENCE: 14
ccagtttact agtgtcatag atcaggagct tagggc                        37

<210> SEQ ID NO 15
<211> LENGTH: 37
<212> TYPE: DNA
<213> ORGANISM: Homo sapiens

<400> SEQUENCE: 15
tgacactagt aaactggctt ctggggtccc atcaagg                       37

<210> SEQ ID NO 16
<211> LENGTH: 97
<212> TYPE: PRT
<213> ORGANISM: Artificial Sequence
<220> FEATURE:
<223> OTHER INFORMATION: Human Murine Chimeric

<400> SEQUENCE: 16

Gln Val Gln Leu Val Gln Ser Gly Ala Glu Val Lys Lys Pro Gly Ala

```
                1               5                   10                  15
Ser Val Lys Val Ser Cys Lys Ala Ser Gly Tyr Thr Phe Asn Ser Tyr
                    20                  25                  30

Tyr Met His Trp Val Arg Gln Ala Pro Gly Gln Gly Leu Glu Trp Met
            35                  40                  45

Gly Ile Ile Asn Pro Ser Gly Ser Thr Ser Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                    85                  90                  95

Ala

<210> SEQ ID NO 17
<211> LENGTH: 117
<212> TYPE: PRT
<213> ORGANISM: Artificial Sequence
<220> FEATURE:
<223> OTHER INFORMATION: Human Murine Chimeric

<400> SEQUENCE: 17

Gln Val Gln Leu Val Gln Ser Gly Ala Glu Val Lys Lys Pro Gly Ala
1               5                   10                  15

Ser Val Lys Val Ser Cys Lys Ala Ser Gly Phe Asn Ile Lys Asp Tyr
                    20                  25                  30

Tyr Ile Tyr Trp Val Arg Gln Ala Pro Gly Gln Gly Leu Glu Trp Ile
            35                  40                  45

Gly Trp Ile Asp Pro Glu Asn Gly Asn Thr Val Phe Asp Pro Lys Phe
    50                  55                  60

Asn Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                    85                  90                  95

Ala Tyr Tyr Gly Thr Ser Ser Phe Asp Phe Trp Gly Gln Gly Thr Thr
                    100                 105                 110

Leu Thr Val Ser Ser
        115

<210> SEQ ID NO 18
<211> LENGTH: 117
<212> TYPE: PRT
<213> ORGANISM: Artificial Sequence
<220> FEATURE:
<223> OTHER INFORMATION: Human Murine Chimeric

<400> SEQUENCE: 18

Glu Val Gln Lys Gln Gln Ser Gly Ala Glu Leu Val Arg Pro Gly Ala
1               5                   10                  15

Leu Val Lys Leu Ser Cys Lys Ala Ser Gly Phe Asn Ile Lys Asp Tyr
                    20                  25                  30

Tyr Ile Tyr Trp Val Lys Gln Arg Pro Glu Gln Gly Leu Glu Trp Ile
            35                  40                  45

Gly Trp Ile Asp Pro Glu Asn Gly Asn Thr Val Phe Asp Pro Leu Phe
    50                  55                  60

Gln Gly Lys Ala Ser Ile Thr Ser Asp Thr Ser Ser Asn Thr Ala Tyr
65                  70                  75                  80

Leu Gln Leu Ser Ser Leu Thr Ser Glu Asp Thr Ala Val Tyr Tyr Cys
                    85                  90                  95
```

Ala Tyr Tyr Gly Thr Ser Ser Phe Asp Phe Trp Gly Gln Gly Thr Thr
            100                 105                 110

Leu Thr Val Ser Ser
        115

<210> SEQ ID NO 19
<211> LENGTH: 95
<212> TYPE: PRT
<213> ORGANISM: Artificial Sequence
<220> FEATURE:
<223> OTHER INFORMATION: Human Murine Chimeric

<400> SEQUENCE: 19

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Ser Trp
            20                  25                  30

Leu Ala Trp Tyr Gln Gln Lys Pro Gly Lys Ala Pro Lys Leu Leu Ile
        35                  40                  45

Tyr Asp Ala Ser Ser Leu Glu Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Tyr Asn Ser Tyr Ser
                85                  90                  95

<210> SEQ ID NO 20
<211> LENGTH: 107
<212> TYPE: PRT
<213> ORGANISM: Artificial Sequence
<220> FEATURE:
<223> OTHER INFORMATION: Human Murine Chimeric

<400> SEQUENCE: 20

Asp Ile Gln Met Thr Gln Ser Pro Ser Thr Leu Ser Ala Ser Val Gly
1               5                   10                  15

Asp Arg Val Thr Ile Thr Cys Lys Ala Ser Gln Asp Ile Asn Arg Tyr
            20                  25                  30

Leu Asn Trp Tyr Gln Gln Lys Pro Gly Lys Ala Pro Lys Leu Leu Ile
        35                  40                  45

Tyr Arg Ala Asn Arg Leu Val Asp Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Leu Gln Phe His Glu Phe Pro Tyr
                85                  90                  95

Thr Phe Gly Gly Gly Thr Lys Leu Glu Ile Leu
            100                 105

<210> SEQ ID NO 21
<211> LENGTH: 107
<212> TYPE: PRT
<213> ORGANISM: Artificial Sequence
<220> FEATURE:
<223> OTHER INFORMATION: Human Murine Chimeric

<400> SEQUENCE: 21

Asp Ile Lys Met Thr Gln Ser Pro Ser Ser Met Tyr Val Ser Leu Gly
1               5                   10                  15

Glu Arg Val Thr Ile Thr Cys Lys Ala Ser Gln Asp Ile Asn Arg Tyr

```
                    20                  25                  30
Leu Asn Trp Phe Gln Gln Lys Pro Gly Lys Ser Pro Lys Thr Leu Ile
            35                  40                  45

His Arg Ala Asn Arg Leu Val Asp Gly Val Pro Ser Arg Phe Ser Gly
    50                  55                  60

Ser Gly Ser Gly Gln Glu Tyr Ser Leu Thr Ile Ser Ser Leu Glu Phe
65                  70                  75                  80

Glu Asp Met Gly Ile Tyr Tyr Cys Leu Gln Phe His Glu Phe Pro Tyr
                85                  90                  95

Thr Phe Gly Gly Gly Thr Lys Leu Glu Ile Leu
            100                 105
```

```
<210> SEQ ID NO 22
<211> LENGTH: 117
<212> TYPE: DNA
<213> ORGANISM: Artificial Sequence
<220> FEATURE:
<223> OTHER INFORMATION: Human Murine Chimeric

<400> SEQUENCE: 22
ccatggactg gacctggagg gtcttctgct tgctggctgt agcaccaggt gcccactccc      60
aggtgcagct ggtgcagtct ggagctgagg tgaagaagcc tggagcctca gtgaagg       117

<210> SEQ ID NO 23
<211> LENGTH: 120
<212> TYPE: DNA
<213> ORGANISM: Artificial Sequence
<220> FEATURE:
<223> OTHER INFORMATION: Human Murine Chimeric

<400> SEQUENCE: 23
cacttcttcg gacctcggag tcacttccaa aggacgttcc gtagacctaa gttgtaattc      60
ctgatgatgt aaatgaccca cgctgtccga ggacctgttc ccgagctcac ctacccaacc    120

<210> SEQ ID NO 24
<211> LENGTH: 119
<212> TYPE: DNA
<213> ORGANISM: Artificial Sequence
<220> FEATURE:
<223> OTHER INFORMATION: Human Murine Chimeric

<400> SEQUENCE: 24
gggctcgagt ggatgggttg gattgaccct gagaatggta atactgtgtt tgaccgaagt      60
tccagggcag agtcaccatg accagggaca cgtccacgag cacagtctac atggagctg     119

<210> SEQ ID NO 25
<211> LENGTH: 137
<212> TYPE: DNA
<213> ORGANISM: Artificial Sequence
<220> FEATURE:
<223> OTHER INFORMATION: Human Murine Chimeric

<400> SEQUENCE: 25
ggtgctcgtg tcagatgtac ctcgactcgt cggactctag actcctgtgc ggcacataa      60 tgacacgcat gatgccatgt tcgaggaaac tgaagacccc ggttccgtgg tgagagtgtc    120
actcgagtat tcctagg                                                  137

<210> SEQ ID NO 26
<211> LENGTH: 106
<212> TYPE: DNA
<213> ORGANISM: Artificial Sequence
```

-continued

```
<220> FEATURE:
<223> OTHER INFORMATION: Human Murine Chimeric

<400> SEQUENCE: 26
ccatggacat gagggtcccc gctcagctcc tggggctcct gctgctctgg ctcccaggtg      60
ccaaatgtga tatccagatg acccagtctc cttccaccct gtctgc                   106

<210> SEQ ID NO 27
<211> LENGTH: 107
<212> TYPE: DNA
<213> ORGANISM: Artificial Sequence
<220> FEATURE:
<223> OTHER INFORMATION: Human Murine Chimeric

<400> SEQUENCE: 27
gtcagaggaa ggtgggacag acgtagacat cctctgtctc agtggtagtg aacgttccgc      60
tcagtcctgt aattatccat aaatttgacc atggtcgtct ttgggcc                  107

<210> SEQ ID NO 28
<211> LENGTH: 107
<212> TYPE: DNA
<213> ORGANISM: Homo sapiens

<400> SEQUENCE: 28
gaaagcccct aagctcctga tctatcgtgc aaacagattg gtagatgggg tcccatcaag      60
gttcagcggc agtggatctg ggacagaatt cactctcacc atcagca                  107

<210> SEQ ID NO 29
<211> LENGTH: 116
<212> TYPE: DNA
<213> ORGANISM: Homo sapiens

<400> SEQUENCE: 29
gtcttaagtg agagtggtag tcgtcggacg tcggactact aaaacgttga ataatgacgg      60
atgtcaaagt actcaaaggc atgtgcaagc ctccccctg gttcgaactt tatttt          116

<210> SEQ ID NO 30
<211> LENGTH: 123
<212> TYPE: PRT
<213> ORGANISM: Artificial Sequence
<220> FEATURE:
<223> OTHER INFORMATION: Human Murine Chimeric

<400> SEQUENCE: 30

Gln Val Thr Leu Arg Glu Ser Gly Pro Ala Leu Val Lys Pro Thr Gln
1               5                   10                  15

Thr Leu Thr Leu Thr Cys Thr Phe Ser Gly Phe Ser Leu Ser Ser Ser
            20                  25                  30

Gly Met Cys Val Gly Trp Ile Arg Gln Pro Pro Gly Lys Ala Leu Glu
        35                  40                  45

Trp Leu Ala Asp Ile Glu Trp Asp Asp Lys Asp Tyr Asn Thr Ser
    50                  55                  60

Leu Asp Thr Arg Leu Thr Ile Ser Lys Asp Thr Ser Lys Asn Gln Val
65                  70                  75                  80

Val Leu Thr Val Thr Asn Met Asp Pro Ala Asp Thr Ala Thr Tyr Tyr
                85                  90                  95

Cys Ala Arg Lys Thr Val Ile Pro Ala Pro Ala Gly Tyr Met Asp Val
            100                 105                 110

Trp Gly Arg Gly Arg Pro Val Thr Val Ser Ser
        115                 120
```

<210> SEQ ID NO 31
<211> LENGTH: 120
<212> TYPE: PRT
<213> ORGANISM: Artificial Sequence
<220> FEATURE:
<223> OTHER INFORMATION: Human Murine Chimeric

<400> SEQUENCE: 31

Gln Val Thr Leu Arg Glu Ser Gly Pro Ala Leu Val Lys Pro Thr Gln
1               5                   10                  15

Thr Leu Thr Leu Thr Cys Thr Phe Ser Gly Phe Ser Leu Ser Thr Ser
            20                  25                  30

Gly Met Ser Val Gly Trp Ile Arg Gln Pro Pro Gly Lys Ala Leu Glu
        35                  40                  45

Trp Leu Ala Asp Ile Trp Trp Asp Asp Lys Lys Asp Tyr Asn Pro Ser
    50                  55                  60

Leu Lys Ser Arg Leu Thr Ile Ser Lys Asp Thr Ser Lys Asn Gln Val
65                  70                  75                  80

Val Leu Lys Val Thr Asn Met Asp Pro Ala Asp Thr Ala Thr Tyr Tyr
                85                  90                  95

Cys Ala Arg Ser Met Ile Thr Asn Trp Tyr Phe Asp Val Trp Gly Ala
            100                 105                 110

Gly Thr Thr Val Thr Val Ser Ser
        115                 120

<210> SEQ ID NO 32
<211> LENGTH: 120
<212> TYPE: PRT
<213> ORGANISM: Artificial Sequence
<220> FEATURE:
<223> OTHER INFORMATION: Human Murine Chimeric

<400> SEQUENCE: 32

Gln Val Glu Leu Gln Glu Ser Gly Pro Gly Ile Leu Gln Pro Ser Gln
1               5                   10                  15

Thr Leu Ser Leu Thr Cys Ser Phe Ser Gly Phe Ser Leu Ser Thr Ser
            20                  25                  30

Gly Met Ser Val Gly Trp Ile Arg Gln Pro Ser Gly Glu Gly Leu Glu
        35                  40                  45

Trp Leu Ala Asp Ile Trp Trp Asp Asp Lys Lys Asp Tyr Asn Pro Ser
    50                  55                  60

Leu Lys Ser Arg Lys Thr Ile Ser Lys Asp Thr Ser Ser Asn Gln Val
65                  70                  75                  80

Phe Leu Lys Ile Thr Gly Val Asp Thr Ala Asp Thr Ala Thr Tyr Tyr
                85                  90                  95

Cys Ala Arg Ser Met Ile Thr Asn Trp Tyr Phe Asp Val Trp Gly Ala
            100                 105                 110

Gly Thr Thr Val Thr Val Ser Ser
        115                 120

<210> SEQ ID NO 33
<211> LENGTH: 95
<212> TYPE: PRT
<213> ORGANISM: Artificial Sequence
<220> FEATURE:
<223> OTHER INFORMATION: Human Murine Chimeric

<400> SEQUENCE: 33

Asp Ile Gln Met Thr Gln Ser Pro Ser Thr Leu Ser Ala Ser Val Gly

```
                1               5                  10                 15
Asp Arg Val Thr Ile Thr Cys Arg Ala Ser Gln Ser Ile Ser Ser Trp
                    20                  25                 30

Leu Ala Trp Tyr Gln Gln Lys Pro Gly Lys Ala Pro Lys Leu Leu Ile
            35                  40                 45

Tyr Asp Ala Ser Ser Leu Glu Ser Gly Val Pro Ser Arg Phe Ser Gly
    50                  55                 60

Ser Gly Ser Gly Thr Glu Phe Thr Leu Thr Ile Ser Ser Leu Gln Pro
65                  70                 75                 80

Asp Asp Phe Ala Thr Tyr Tyr Cys Gln Gln Tyr Asn Ser Tyr Ser
                85                  90                 95
```

<210> SEQ ID NO 34
<211> LENGTH: 106
<212> TYPE: PRT
<213> ORGANISM: Artificial Sequence
<220> FEATURE:
<223> OTHER INFORMATION: Human Murine Chimeric

<400> SEQUENCE: 34

```
Asp Ile Gln Met Thr Gln Ser Pro Ser Thr Leu Ser Ala Ser Val Gly
1               5                  10                 15

Asp Arg Val Thr Ile Thr Cys Lys Cys Gln Leu Ser Val Gly Tyr Met
                    20                  25                 30

His Trp Tyr Gln Gln Lys Pro Gly Lys Ala Pro Lys Leu Trp Ile Tyr
            35                  40                 45

Asp Thr Ser Lys Leu Ala Ser Gly Val Pro Ser Arg Phe Ser Gly Ser
    50                  55                 60

Gly Ser Gly Thr Glu Phe Thr Leu Thr Ile Ser Ser Leu Gln Pro Asp
65                  70                 75                 80

Asp Phe Ala Thr Tyr Tyr Cys Phe Gln Gly Ser Gly Tyr Pro Phe Thr
                85                  90                 95

Phe Gly Gly Gly Thr Lys Leu Glu Ile Lys
                100                 105
```

<210> SEQ ID NO 35
<211> LENGTH: 106
<212> TYPE: PRT
<213> ORGANISM: Artificial Sequence
<220> FEATURE:
<223> OTHER INFORMATION: Human Murine Chimeric

<400> SEQUENCE: 35

```
Asp Ile Gln Leu Thr Gln Ser Pro Ala Ile Met Ser Ala Ser Pro Gly
1               5                  10                 15

Glu Lys Val Thr Met Thr Cys Ser Ala Ser Ser Ser Val Gly Tyr Met
                    20                  25                 30

His Trp Tyr Gln Gln Lys Ser Ser Thr Ser Pro Lys Leu Trp Ile Tyr
            35                  40                 45

Asp Thr Ser Lys Leu Ala Ser Gly Val Pro Gly Arg Phe Ser Gly Ser
    50                  55                 60

Gly Ser Gly Asn Ser Tyr Ser Leu Thr Ile Ser Ser Ile Gln Ala Glu
65                  70                 75                 80

Asp Val Ala Thr Tyr Tyr Cys Phe Gln Gly Ser Gly Tyr Pro Phe Thr
                85                  90                 95

Phe Gly Gly Gly Thr Lys Leu Glu Ile Lys
                100                 105
```

```
<210> SEQ ID NO 36
<211> LENGTH: 62
<212> TYPE: DNA
<213> ORGANISM: Homo sapiens

<400> SEQUENCE: 36
gcctgagctc acggtgaccg tggtcccgcc gccccagaca tcgaagtagc agttcgtgat    60
ca                                                                   62

<210> SEQ ID NO 37
<211> LENGTH: 60
<212> TYPE: DNA
<213> ORGANISM: Homo sapiens

<400> SEQUENCE: 37
gttggtgact ttaaggacca cctggttttt ggaggtatcc ttggagattg tgagccggct    60

<210> SEQ ID NO 38
<211> LENGTH: 60
<212> TYPE: DNA
<213> ORGANISM: Homo sapiens

<400> SEQUENCE: 38
gcgccttccc tgggggctga cgaatccagc ctacactcat accagaagtg ctcagtgaaa    60

<210> SEQ ID NO 39
<211> LENGTH: 70
<212> TYPE: DNA
<213> ORGANISM: Homo sapiens

<400> SEQUENCE: 39
ccaggtcacc ttaagggagt ctggtcctgc gctggtgaaa cccacacaga ccctcacact    60
gacctgcacc                                                           70

<210> SEQ ID NO 40
<211> LENGTH: 78
<212> TYPE: DNA
<213> ORGANISM: Homo sapiens

<400> SEQUENCE: 40
cagcccccag ggaaggccct ggagtcgctt gcagacattt ggtgggatga caaaaaggac    60
tataatccat ccctgaag                                                  78

<210> SEQ ID NO 41
<211> LENGTH: 64
<212> TYPE: DNA
<213> ORGANISM: Homo sapiens

<400> SEQUENCE: 41
ggtccttaaa gtgaccaaca tggaccctgc tgatactgcc acttactact gtgctcggtc    60
tatg                                                                 64

<210> SEQ ID NO 42
<211> LENGTH: 72
<212> TYPE: DNA
<213> ORGANISM: Homo sapiens

<400> SEQUENCE: 42
ggcgtcgact caccatggac tggacctgga gggtcttctg cttgctggct gtagcaccag    60
gtgcccactc cc                                                        72
```

```
<210> SEQ ID NO 43
<211> LENGTH: 7
<212> TYPE: PRT
<213> ORGANISM: Murine

<400> SEQUENCE: 43

Thr Ser Gly Met Ser Val Gly
1               5

<210> SEQ ID NO 44
<211> LENGTH: 16
<212> TYPE: PRT
<213> ORGANISM: Murine

<400> SEQUENCE: 44

Asp Ile Trp Trp Asp Asp Lys Lys Asp Tyr Asn Pro Ser Leu Lys Ser
1               5                   10                  15

<210> SEQ ID NO 45
<211> LENGTH: 10
<212> TYPE: PRT
<213> ORGANISM: Murine

<400> SEQUENCE: 45

Ser Met Ile Thr Asn Trp Tyr Phe Asp Val
1               5                   10

<210> SEQ ID NO 46
<211> LENGTH: 10
<212> TYPE: PRT
<213> ORGANISM: Artificial Sequence
<220> FEATURE:
<223> OTHER INFORMATION: Human Murine Chimeric

<400> SEQUENCE: 46

Lys Cys Gln Leu Ser Val Gly Tyr Met His
1               5                   10

<210> SEQ ID NO 47
<211> LENGTH: 7
<212> TYPE: PRT
<213> ORGANISM: Murine

<400> SEQUENCE: 47

Asp Thr Ser Lys Leu Ala Ser
1               5

<210> SEQ ID NO 48
<211> LENGTH: 9
<212> TYPE: PRT
<213> ORGANISM: Murine

<400> SEQUENCE: 48

Phe Gln Gly Ser Gly Tyr Pro Phe Thr
1               5

<210> SEQ ID NO 49
<211> LENGTH: 6
<212> TYPE: PRT
<213> ORGANISM: Murine

<400> SEQUENCE: 49

Ser Val Gly Tyr Met His
1               5
```

What is claimed is:

1. A method of neutralizing respiratory syncytial virus (RSV), comprising administering to a human in need thereof an effective amount of a humanized anti-RSV antibody comprising
   (a) a variable heavy chain polypeptide comprising a VH CDR1 comprising the amino acid sequence of SEQ ID NO: 43, a VH CDR2 comprising the amino acid sequence of SEQ ID NO: 44, and a VH CDR3 comprising the amino acid sequence of SEQ ID NO: 45; and
   a variable light chain polypeptide comprising a VL CDR1 comprising the amino acid sequence of SEQ ID NO: 46, a VL CDR2 comprising the amino acid sequence of SEQ ID NO: 47, and a VL CDR3 comprising the amino acid sequence of SEQ ID NO: 48; or
   (b) a variable heavy chain polypeptide and a variable light chain polypeptide, wherein the variable heavy chain polypeptide sequence is SEQ ID NO:31 and the variable light chain polypeptide sequence is SEQ ID NO:34.

2. A method of neutralizing respiratory syncytial virus (RSV), comprising administering to a human in need thereof a pharmaceutical composition comprising an effective amount of a humanized anti-RSV antibody in conjunction with an acceptable pharmaceutical carrier, wherein the humanized anti-RSV antibody comprises:
   (a) a variable heavy chain polypeptide comprising a VH CDR1 comprising the amino acid sequence of SEQ ID NO: 43, a VH CDR2 comprising the amino acid sequence of SEQ ID NO: 44, and a VH CDR3 comprising the amino acid sequence of SEQ ID NO: 45; and
   a variable light chain polypeptide comprising a VL CDR1 comprising the amino acid sequence of SEQ ID NO: 46, a VL CDR2 comprising the amino acid sequence of SEQ ID NO: 47, and a VL CDR3 comprising the amino acid sequence of SEQ ID NO: 48; or
   (b) a variable heavy chain polypeptide and a variable light chain polypeptide, wherein the variable heavy chain polypeptide sequence is SEQ ID NO:31 and the variable light chain polypeptide sequence is SEQ ID NO:34.

3. The method of claim 1, wherein the humanized anti-RSV antibody comprises:
   (a) a variable heavy chain polypeptide comprising a VH CDR1 comprising the amino acid sequence of SEQ ID NO: 43, a VH CDR2 comprising the amino acid sequence of SEQ ID NO: 44, and a VH CDR3 comprising the amino acid sequence of SEQ ID NO: 45; and
   (b) a variable light chain polypeptide comprising a VL CDR1 comprising the amino acid sequence of SEQ ID NO: 46, a VL CDR2 comprising the amino acid sequence of SEQ ID NO: 47, and a VL CDR3 comprising the amino acid sequence of SEQ ID NO: 48.

4. The method of claim 1, wherein the humanized anti-RSV antibody comprises a variable heavy chain polypeptide and a variable light chain polypeptide, wherein the variable heavy chain polypeptide sequence is SEQ ID NO:31 and the variable light chain polypeptide sequence is SEQ ID NO:34.

5. The method of claim 2, wherein the humanized anti-RSV antibody comprises:
   (a) a variable heavy chain polypeptide comprising a VH CDR1 comprising the amino acid sequence of SEQ ID NO: 43, a VH CDR2 comprising the amino acid sequence of SEQ ID NO: 44, and a VH CDR3 comprising the amino acid sequence of SEQ ID NO: 45; and
   (b) a variable light chain polypeptide comprising a VL CDR1 comprising the amino acid sequence of SEQ ID NO: 46, a VL CDR2 comprising the amino acid sequence of SEQ ID NO: 47, and a VL CDR3 comprising the amino acid sequence of SEQ ID NO: 48.

6. The method of claim 2, wherein the humanized anti-RSV antibody comprises a variable heavy chain polypeptide and a variable light chain polypeptide, wherein the variable heavy chain polypeptide sequence is SEQ NO:31 and the variable light chain polypeptide sequence is SEQ ID NO:34.

7. The method of claim 3, wherein the humanized antibody is administered intramuscularly.

8. The method of claim 4, wherein the humanized antibody is administered intramuscularly.

9. The method of claim 5, wherein the pharmaceutical composition is administered intramuscularly.

10. The method of claim 6, wherein the pharmaceutical composition is administered intramuscularly.

* * * * *